United States Patent
Fostick et al.

(10) Patent No.: US 10,898,716 B2
(45) Date of Patent: *Jan. 26, 2021

(54) ELECTRICAL SUBSTANCE CLEARANCE FROM THE BRAIN

(71) Applicant: RAINBOW MEDICAL LTD., Herzliya (IL)

(72) Inventors: Gideon Fostick, Givat Shmuel (IL); Yossi Gross, Moshav Mazor (IL); Alex Tendler, Haifa (IL)

(73) Assignee: RAINBOW MEDICAL LTD., Herzliya (IL)

(*) Notice: Subject to any disclaimer, the term of this patent is extended or adjusted under 35 U.S.C. 154(b) by 113 days.

This patent is subject to a terminal disclaimer.

(21) Appl. No.: 15/771,551

(22) PCT Filed: Oct. 27, 2016

(86) PCT No.: PCT/IL2016/051161
§ 371 (c)(1),
(2) Date: Apr. 27, 2018

(87) PCT Pub. No.: WO2017/072769
PCT Pub. Date: May 4, 2017

(65) Prior Publication Data
US 2019/0076653 A1 Mar. 14, 2019

Related U.S. Application Data

(63) Continuation-in-part of application No. 14/926,705, filed on Oct. 29, 2015, now Pat. No. 9,724,515.

(51) Int. Cl.
*A61N 1/00* (2006.01)
*A61N 1/36* (2006.01)
(Continued)

(52) U.S. Cl.
CPC ....... *A61N 1/36082* (2013.01); *A61N 1/0529* (2013.01); *A61N 1/0504* (2013.01); *A61N 1/0534* (2013.01); *A61N 1/306* (2013.01)

(58) Field of Classification Search
CPC ...... A61N 1/36082; A61N 1/30; A61N 1/325; A61N 1/3606; A61N 1/0529; A61N 1/0534; A61N 1/0504; A61N 1/306
See application file for complete search history.

(56) References Cited

U.S. PATENT DOCUMENTS

| | | |
|---|---|---|
| 4,044,774 A | 8/1977 | Corbin et al. |
| 4,503,863 A | 3/1985 | Katims |

(Continued)

FOREIGN PATENT DOCUMENTS

| | | |
|---|---|---|
| JP | 2004-321242 A | 11/2004 |
| JP | 2007-501067 A | 1/2007 |

(Continued)

OTHER PUBLICATIONS

Karran September E et201 al., 1 "The Amyloid cascade hypothesis for AD," Nature Reviews Drug Discovery, vol. 10; 698-712.

(Continued)

*Primary Examiner* — Scott M. Getzow
(74) *Attorney, Agent, or Firm* — Sughrue Mion, PLLC

(57) ABSTRACT

A method is provided that includes implanting (a) a parenchymal electrode in or in contact with an outer surface of brain parenchyma of a subject identified as at risk of or suffering from a disease, and (b) a cerebrospinal fluid (CSF) electrode in a CSF-filled space of a brain of the subject, the CSF-filled space selected from the group consisting of: a ventricular system and a subarachnoid space. A midplane treatment electrode is disposed in or over a superior sagittal sinus. Control circuitry is activated to drive the parenchymal electrode and the CSF electrode to drive a substance from (Continued)

the brain parenchyma into the CSF-filled space of the brain, and apply a treatment current between the CSF electrode and the midplane treatment electrode to drive the substance from the CSF-filled space of the brain to the superior sagittal sinus. Other embodiments are also described.

32 Claims, 12 Drawing Sheets

(51) Int. Cl.
A61N 1/05 (2006.01)
A61N 1/30 (2006.01)

(56) References Cited

U.S. PATENT DOCUMENTS

| | | |
|---|---|---|
| 5,088,977 A | 2/1992 | Sibalis |
| 5,121,754 A | 6/1992 | Mullett |
| 5,433,739 A | 7/1995 | Sluijter et al. |
| 5,529,574 A | 6/1996 | Frackelton |
| 5,792,100 A | 8/1998 | Shantha |
| 5,911,223 A | 6/1999 | Weaver et al. |
| 5,938,690 A | 8/1999 | Law et al. |
| 6,041,252 A | 3/2000 | Walker et al. |
| 6,146,380 A | 11/2000 | Racz et al. |
| 6,161,047 A | 12/2000 | King et al. |
| 6,360,750 B1 | 3/2002 | Gerber et al. |
| 6,567,702 B1 | 5/2003 | Nekhendzy et al. |
| 6,591,138 B1 | 7/2003 | Fischell et al. |
| 6,602,248 B1 | 8/2003 | Sharps et al. |
| 6,620,155 B2 | 9/2003 | Underwood et al. |
| 6,941,172 B2 | 9/2005 | Nachum |
| 6,997,941 B2 | 2/2006 | Sharkey et al. |
| 7,013,177 B1 | 3/2006 | Whitehurst et al. |
| 7,120,489 B2 | 10/2006 | Shalev et al. |
| 7,217,351 B2 | 5/2007 | Krumme |
| 7,223,227 B2 | 5/2007 | Pflueger |
| 7,270,659 B2 | 9/2007 | Ricart et al. |
| 7,317,947 B2 | 1/2008 | Wahlstrand et al. |
| 7,398,121 B2 | 7/2008 | Matsumura et al. |
| 7,509,171 B2 | 3/2009 | DiMauro |
| 7,640,062 B2 | 12/2009 | Shalev |
| 7,818,063 B2 | 10/2010 | Wallace et al. |
| 7,831,306 B2 | 11/2010 | Finch et al. |
| 7,860,569 B2 | 12/2010 | Solberg et al. |
| 8,060,207 B2 | 11/2011 | Wallace et al. |
| 8,190,248 B2 | 5/2012 | Besio et al. |
| 8,353,853 B1 | 1/2013 | Kyle et al. |
| 8,457,761 B2 | 6/2013 | Wariar |
| 8,577,469 B2 | 11/2013 | Gross |
| 8,676,348 B2 | 3/2014 | Gross |
| 8,731,674 B2 | 5/2014 | Wallace et al. |
| 9,616,221 B2 | 4/2017 | Gross |
| 9,724,513 B2 | 8/2017 | Lane et al. |
| 9,724,515 B2 * | 8/2017 | Fostick ............... A61N 1/0529 |
| 9,731,122 B2 | 8/2017 | Gross |
| 10,398,884 B2 | 9/2019 | Lad et al. |
| 2002/0151948 A1 | 10/2002 | King et al. |
| 2002/0183683 A1 | 12/2002 | Lerner |
| 2003/0130707 A1 | 7/2003 | Gan et al. |
| 2003/0158589 A1 | 8/2003 | Katsnelson |
| 2003/0216792 A1 | 11/2003 | Levin et al. |
| 2003/0225331 A1 | 12/2003 | Diederich et al. |
| 2004/0002746 A1 | 1/2004 | Ryan et al. |
| 2004/0019381 A1 | 1/2004 | Pflueger |
| 2004/0049180 A1 | 3/2004 | Sharps et al. |
| 2004/0116977 A1 | 6/2004 | Finch et al. |
| 2004/0210209 A1 | 10/2004 | Yeung et al. |
| 2005/0010205 A1 | 1/2005 | Hovda et al. |
| 2005/0021104 A1 | 1/2005 | DiLorenzo |
| 2005/0119650 A1 | 6/2005 | Sanders et al. |
| 2005/0137646 A1 | 6/2005 | Wallace et al. |
| 2005/0159790 A1 | 7/2005 | Shalev |
| 2005/0187589 A1 | 8/2005 | Wallace et al. |
| 2005/0203599 A1 | 9/2005 | Garabedian et al. |
| 2005/0203600 A1 | 9/2005 | Wallace et al. |
| 2005/0203602 A1 | 9/2005 | Wallace et al. |
| 2005/0222647 A1 | 10/2005 | Wahlstrand et al. |
| 2005/0277996 A1 | 12/2005 | Podhajsky et al. |
| 2006/0030895 A1 | 2/2006 | Simon et al. |
| 2006/0106430 A1 | 5/2006 | Fowler et al. |
| 2006/0224223 A1 | 10/2006 | Podhajsky et al. |
| 2006/0293723 A1 | 12/2006 | Whitehurst et al. |
| 2007/0000784 A1 | 1/2007 | Paul et al. |
| 2007/0073402 A1 | 3/2007 | Vresilovic et al. |
| 2007/0162086 A1 | 7/2007 | Dilorenzo |
| 2007/0213700 A1 | 9/2007 | Davison et al. |
| 2007/0255338 A1 | 11/2007 | Wahlstrand |
| 2008/0009927 A1 | 1/2008 | Vilims |
| 2008/0119907 A1 | 5/2008 | Stahmann |
| 2008/0260542 A1 | 10/2008 | Nishikawa et al. |
| 2009/0112278 A1 | 4/2009 | Wingeier et al. |
| 2009/0125080 A1 | 5/2009 | Montgomery |
| 2009/0126813 A1 | 5/2009 | Yanagisawa et al. |
| 2009/0131850 A1 | 5/2009 | Geiger |
| 2009/0312816 A1 | 12/2009 | Gross |
| 2010/0217369 A1 | 8/2010 | Gross |
| 2010/0324441 A1 | 12/2010 | Hargrove et al. |
| 2011/0046540 A1 | 2/2011 | Alterman et al. |
| 2011/0054518 A1 | 3/2011 | Carbunaru et al. |
| 2011/0160638 A1 | 6/2011 | Mauge et al. |
| 2011/0160797 A1 | 6/2011 | Makous et al. |
| 2012/0053659 A1 | 3/2012 | Molnar et al. |
| 2012/0203307 A1 | 8/2012 | Schroeppel et al. |
| 2013/0066392 A1 | 3/2013 | Simon et al. |
| 2013/0102952 A1 | 4/2013 | Gross |
| 2013/0166006 A1 | 6/2013 | Williams |
| 2013/0289385 A1 | 10/2013 | Lozano et al. |
| 2014/0058189 A1 | 2/2014 | Stubbeman |
| 2014/0088672 A1 | 3/2014 | Bedenbaugh |
| 2014/0207224 A1 | 7/2014 | Simon |
| 2014/0257168 A1 | 9/2014 | Gill |
| 2014/0324128 A1 | 10/2014 | Gross |
| 2015/0011927 A1 | 1/2015 | Hua |
| 2015/0119898 A1 | 4/2015 | Desalles et al. |
| 2016/0331970 A1 | 11/2016 | Lozano |
| 2017/0007823 A1 * | 1/2017 | Gross ....................... A61N 1/30 |
| 2017/0056642 A1 | 3/2017 | Moffitt et al. |
| 2017/0120053 A1 | 5/2017 | Fostick et al. |
| 2017/0182317 A1 | 6/2017 | Gross et al. |
| 2017/0296821 A1 | 10/2017 | Fostick et al. |
| 2018/0071523 A1 | 3/2018 | Gross et al. |

FOREIGN PATENT DOCUMENTS

| | | |
|---|---|---|
| WO | 94/05369 | 3/1994 |
| WO | 01/52931 | 7/2001 |
| WO | 01/85027 | 11/2001 |
| WO | 2001/085094 | 11/2001 |
| WO | 2005/011805 A2 | 2/2005 |
| WO | 2006/090397 | 8/2006 |
| WO | 2008/007369 | 1/2008 |
| WO | 2017/006327 | 1/2017 |
| WO | 2017/072769 | 5/2017 |
| WO | 2017/115351 | 7/2017 |
| WO | 2018/051338 | 3/2018 |

OTHER PUBLICATIONS

De La Tone JC, "Vascular Basis of Alzheimer's Pathogensis," Ann NY Acad Sci. 977:196-215 (Nov. 2002).
Weller RO et al, "Perivascular Drainage of Amyloid-b Peptides from the Brain and Its Failure in Cerebral Amyloid Angiopathy and Alzheimer's Disease," Brain Pathology 18 (Apr. 2008) 253-266.
Brief PubMed search for metal ions in Alzheimers.
An Office Action dated Sep. 27, 2016, which issued during the prosecution of U.S. Appl. No. 14/926,705.
An International Search Report and a Written Opinion both dated Aug. 7, 2008, which issued during the prosecution of Applicant's PCT/IL2007/000865.
An Office Action dated Mar. 29, 2013, which issued during the prosecution of U.S. Appl. No. 12/373,306.

(56) References Cited

OTHER PUBLICATIONS

An Office Action dated Oct. 31, 2011, which issued during the prosecution of U.S. Appl. No. 12/373,306.
An Office Action dated Oct. 1, 2012, which issued during the prosecution of U.S. Appl. No. 12/373,306.
Notice of Allowance dated Jul. 24, 2013. which issued during the prosecution of U.S. Appl. No. 12/373,306.
An Office Action dated Apr. 11, 2013, which issued during the prosecution of U.S. Appl. No. 13/663,757.
Notice of Allowance dated Oct. 28, 2013, which issued during the prosecution of U.S. Appl. No. 13/663,757.
Elixmann IM et al., "In-vitro evaluation of a drainage catheter with integrated bioimpedance electrodes to determine ventricular size," Biomed Tech 2013; 58 (Suppl. 1) Sep. 2013 (2 pages total).
An Office Action dated Aug. 31, 2015, which issued during the prosecution of U.S. Appl. No. 13/872,794.
An Applicant Initiated Interview Summary dated Dec. 14, 2015, which of issued during the prosecution of U.S. Appl. No. 13/872,794.
An Office Action dated Feb. 3, 2016, which issued during the prosecution of U.S. Appl. No. 13/872,794.
Notice of Allowance dated Dec. 9, 2016, which issued during the prosecution of U.S. Appl. No. 14/794,739.
An Applicant Initiated Interview Summary dated Feb. 25, 2016, which issued during the prosecution of U.S. Appl. No. 13/872,794.
An Office Action dated Jun. 15, 2016, which issued during the prosecution of U.S. Appl. No. 13/872,794.
An International Search Report and a Written Opinion both dated Oct. 20, 2016, which issued during the prosecution of Applicant's PCT/IL2016/050728.
An Office Action dated Sep. 21, 2016, which issued during the prosecution of U.S. Appl. No. 14/794,739.
An International Search Report and a Written Opinion both dated Jan. 26, 2017, which issued during the prosecution of Applicant's PCT/IL2016/051161.
Notice of Allowance dated Jul. 14, 2017, which issued during the prosecution of U.S. Appl. No. 13/872,794.
An Office Action dated May 26, 2017, which issued during the prosecution of U.S. Appl. No. 15/453,290.
An International Preliminary Report on Patentability dated Apr. 7, 2009, which issued during the prosecution of Applicant's PCT/IL2007/000865.
Loutzenhiser, "Membrane Potential measurements in renal afferent and efferent arterioles: actions of Angiotensin II", AJP—Renal Physiol Aug. 1, 1997 vol. 273 No. 2 F307-F314.
U.S. Appl. No. 60/830,717, filed Jul. 12, 2006.
Dao-Sheng Liu et al., "Activation of Na+ and K+ Pumping Modes of (Na,K)-ATPase by an Oscillating Electric Field," the Journal of Biological Chemistry, vol. 265. No. 13, May 5, 1990. (pp. 7260-7267).

Robert F. Service.. "Electric fields deliver drugs into tumors." http://news.sciencemaa.ora. Feb. 4, 2015. (5 Pages Total).
Vernengo J, "Injectable Bioadhesive Hydrogels for Nucleus Pulposus Replacement and Repair of the Damaged Intervertebral Disc: A Thesis," Drexel University (Jan. 2007).
Urban JPG et al., "The nucleus of the intervertebral disc from development to degeneration," American Zoologist 40(1): 53-61 (2000).
Cheung KMC et al., "Intervertebral disc regeneration by use of autologous mesenchymal stem cells, an experimental model in rabbits, " Abstract from the SRS 2004 Annual Meeting.
Freemont TJ et al., "Degeneration of intervertebral discs: current understanding of cellular and molecular events, and implications for novel therapies," Expert Reviews in Molecular Biology, Mar. 29, 2001 (Cambridge University Press).
An Office Action dated Sep. 12, 2011, which issued during the prosecution of U.S. Appl. No. 12/373,306.
An Office Action dated Jul. 24, 2017. which issued during the prosecution of U.S. Appl. No. 14/982,187.
An International Search Report and a Written Opinion both dated Mar. 10, 2017, which issued during the prosecution of Applicant's PCT/IL2016/051363.
An Office Action dated Apr. 25, 2018, which issued during the prosecution of U.S. Appl. No. 15/637,330.
U.S. Appl. No. 62/444,939, filed Jan. 11, 2017.
An Office Action dated Jul. 29, 2019, which issued during the prosecution of U.S. Appl. No. 15/618,325.
An Office Action dated Jul. 10, 2019, which issued during the prosecution of U.S. Appl. No. 15/864,065.
An International Search Report and a Written Opinion both dated May 23, 2019, which issued during the prosecution of Applicants PCT/IL2019/050284.
An Office Action dated Mar. 25, 2019, which issued during the prosecution of U.S. Appl. No. 15/742,245.
Sawyer, P N et al. "Measurement of streaming potentials of mammalian blood vessels, aorta and vena cava, in vivo." Biophysical journal vol. 6,5 (1966): 641-51. doi:10.1016/50006-3495(66)86683-3, https://www.ncbi.nlm.nih.gov/pmc/articles/PMC1368020/, viewed on Jul. 22, 2019.
A non-final office action issued in U.S. Appl. No. 15/969,411, dated Nov. 29, 2019.
A non-final office action issued in U.S. Appl. No. 15/618,325, dated Jan. 7, 2020.
A Communication in European Appl. 16741703.9, dated Jan. 7, 2020.
A non-final office action issued in U.S. Appl. No. 15/618,325, dated Mar. 6, 2020.
Communication dated Aug. 25, 2020, issued by the Japanese Patent Office in application No. 2018-521586.
A Non-Final Office Action issued in U.S. Appl. No. 16/353,407, dated Nov. 20, 2020.

\* cited by examiner

ELECTRICAL SUBSTANCE CLEARANCE FROM THE BRAIN

CROSS-REFERENCE TO RELATED APPLICATIONS

The present application is the U.S. national stage of International Application PCT/IL2016/051161, filed Oct. 27, 2016, which claims priority from and is a continuation-in-part of U.S. application Ser. No. 14/926,705, filed Oct. 29, 2015, now U.S. Pat. No. 9,724,515, which is assigned to the assignee of the present application and is incorporated herein by reference.

FIELD OF THE APPLICATION

The present invention relates generally to treatment and prevention of Alzheimer's disease and/or cerebral amyloid angiopathy (CAA), and specifically to electrical techniques for treating, preventing, or slowing the progression of Alzheimer's disease and/or CAA.

BACKGROUND OF THE APPLICATION

Alzheimer's disease is a chronic neurodegenerative disease that causes dementia. Accumulation of substances such as amyloid beta and/or tau protein in the brain is widely believed to contribute to the development of Alzheimer's disease.

US Patent Application Publication 2014/0324128 to Gross, which is assigned to the assignee of the present application and is incorporated herein by reference, describes apparatus for driving fluid between first and second anatomical sites of a subject. The apparatus comprises (1) a first electrode, configured to be coupled to the first anatomical site of the subject; (2) a second electrode, configured to be coupled to the second anatomical site of the subject; and (3) a control unit, configured to (i) detect a pressure difference between the first and second anatomical sites, and (ii) in response to the detected pressure difference, drive fluid between the first and second anatomical sites by applying a treatment voltage between the first and second electrodes. Other embodiments are also described.

SUMMARY OF THE APPLICATION

Some embodiments of the present invention provide techniques for treating Alzheimer's disease and/or cerebral amyloid angiopathy (CAA). In some applications of the present invention, a parenchymal electrode is implanted in parenchyma of the brain, and a cerebrospinal fluid (CSF) electrode is implanted in a CSF-filled space of the brain, e.g., selected from a ventricular system and a subarachnoid space. Control circuitry is activated to drive the parenchymal and the CSF electrodes to clear a substance, such as amyloid beta and/or tau protein, from the brain parenchyma into the CSF-filled space of the brain.

In some applications, the techniques of the present invention, in addition to clearing the substance from the brain parenchyma into the CSF-filled space, clear the substance from the CSF-filled space to a superior sagittal sinus of the brain.

There is therefore provided, in accordance with an inventive concept 1 of the present invention, apparatus comprising:

a parenchymal electrode, configured to be implanted in brain parenchyma of a subject identified as at risk of or suffering from a disease;

a cerebrospinal fluid (CSF) electrode, configured to be implanted in a CSF-filled space of a brain of the subject, the CSF-filled space selected from the group consisting of: a ventricular system and a subarachnoid space; and control circuitry, configured to drive the parenchymal and the CSF electrodes to clear a substance from the brain parenchyma into the CSF-filled space of the brain.

There is further provided, in accordance with an inventive concept 2 of the present invention, apparatus comprising:

a parenchymal electrode, configured to be implanted in electrical contact with brain parenchyma of a subject identified as at risk of or suffering from a disease;

a cerebrospinal fluid (CSF) electrode, configured to be implanted in a CSF-filled space of a brain of the subject, the CSF-filled space selected from the group consisting of: a ventricular system and a subarachnoid space; and control circuitry, configured to drive the parenchymal and the CSF electrodes to clear a substance from the brain parenchyma into the CSF-filled space of the brain.

Inventive concept 3. The apparatus according to any one of inventive concepts 1-2, wherein the disease is Alzheimer's disease, and wherein the parenchymal electrode is configured to be implanted in the subject identified as at risk of or suffering from Alzheimer's disease.

Inventive concept 4. The apparatus according to any one of inventive concepts 1-2, wherein the disease is cerebral amyloid angiopathy (CAA), and wherein the parenchymal electrode is configured to be implanted in the subject identified as at risk of or suffering from CAA.

Inventive concept 5. The apparatus according to any one of inventive concepts 1-2, wherein the CSF-filled space of the brain is the ventricular system, and wherein the CSF electrode is a ventricular electrode, configured to be implanted in the ventricular system.

Inventive concept 6. The apparatus according to any one of inventive concepts 1-2, wherein the CSF-filled space of the brain is the subarachnoid space, and wherein the CSF electrode is a subarachnoid electrode, configured to be implanted in the subarachnoid space.

Inventive concept 7. The apparatus according to any one of inventive concepts 1-2, wherein the substance includes amyloid beta, and wherein the control circuitry is configured to drive the parenchymal and the CSF electrodes to clear the amyloid beta from the brain parenchyma into the CSF-filled space of the brain.

Inventive concept 8. The apparatus according to any one of inventive concepts 1-2, wherein the substance includes metal ions, and wherein the control circuitry is configured to drive the parenchymal and the CSF electrodes to clear the metal ions from the brain parenchyma into the CSF-filled space of the brain.

Inventive concept 9. The apparatus according to any one of inventive concepts 1-2, wherein the substance includes tau protein, and wherein the control circuitry is configured to drive the parenchymal and the CSF electrodes to clear the tau protein from the brain parenchyma into the CSF-filled space of the brain.

Inventive concept 10. The apparatus according to any one of inventive concepts 1-2, wherein the parenchymal electrode is configured to be implanted in white matter of the brain.

Inventive concept 11. The apparatus according to any one of inventive concepts 1-2, wherein the control circuitry is configured to configure the parenchymal electrode to be an anode, and the CSF electrode to be a cathode.

Inventive concept 12. The apparatus according to any one of inventive concepts 1-2, wherein the control circuitry is configured to configure the parenchymal electrode to be a cathode, and the CSF electrode to be an anode.

Inventive concept 13. The apparatus according to any one of inventive concepts 1-2, wherein the control circuitry is configured to additionally apply deep brain stimulation using the parenchymal electrode.

Inventive concept 14. The apparatus according to any one of inventive concepts 1-2, wherein the control circuitry is configured to be implanted under skin of the subject.

Inventive concept 15. The apparatus according to any one of inventive concepts 1-2, wherein the control circuitry is configured to drive the parenchymal and the CSF electrodes to clear the substance by applying a non-excitatory current between the parenchymal and the CSF electrodes.

Inventive concept 16. The apparatus according to any one of inventive concepts 1-2, wherein the control circuitry is configured to drive the parenchymal and the CSF electrodes to clear the substance by applying direct current between the parenchymal and the CSF electrodes.

Inventive concept 17. The apparatus according to inventive concept 16, wherein the control circuitry is configured to apply the direct current with an average amplitude of between 1 and 5 mA.

Inventive concept 18. The apparatus according to inventive concept 16, wherein the control circuitry is configured to apply the direct current with an average amplitude of less than 1.2 V.

Inventive concept 19. The apparatus according to inventive concept 16, wherein the control circuitry is configured to apply the direct current as a series of pulses.

Inventive concept 20. The apparatus according to inventive concept 19, wherein the control circuitry is configured to apply the direct current as the series of pulses having an average pulse duration of between 100 milliseconds and 300 seconds.

Inventive concept 21. The apparatus according to inventive concept 19, wherein the control circuitry is configured to apply the direct current as the series of pulses with a duty cycle of between 1% and 50%.

Inventive concept 22. The apparatus according to inventive concept 19, wherein the control unit is configured to:
 drive the parenchymal and the CSF electrodes to clear the substance by applying a voltage between the parenchymal and the CSF electrodes during each of the pulses,
 while applying the voltage, measure a current resulting from application of the voltage during the pulse, and
 terminate the pulse upon the measured current falling below a threshold value.

Inventive concept 23. The apparatus according to inventive concept 22, wherein the threshold value is based on an initial current magnitude measured upon commencement of the pulse.

Inventive concept 24. The apparatus according to any one of inventive concepts 1-2, further comprising a midplane treatment electrode, adapted to be disposed in or over a superior sagittal sinus, wherein the control circuitry is configured to clear the substance from the CSF-filled space of the brain to the superior sagittal sinus, by applying a treatment current between the midplane treatment electrode and the CSF electrode.

Inventive concept 25. The apparatus according to inventive concept 24, wherein the midplane treatment electrode is adapted to be disposed over the superior sagittal sinus.

Inventive concept 26. The apparatus according to inventive concept 25, wherein the midplane treatment electrode is adapted to be disposed over the superior sagittal sinus, outside and in electrical contact with a skull of a head of the subject.

Inventive concept 27. The apparatus according to inventive concept 25, wherein the midplane treatment electrode is adapted to be disposed over the superior sagittal sinus, under a skull of a head of the subject.

Inventive concept 28. The apparatus according to inventive concept 24, wherein the midplane treatment electrode is adapted to be implanted in the superior sagittal sinus.

Inventive concept 29. The apparatus according to inventive concept 24, wherein the CSF electrode is adapted to be disposed between 1 and 12 cm of a sagittal midplane of a skull of the subject.

Inventive concept 30. The apparatus according to inventive concept 24,
 wherein the CSF-filled space of the brain is the subarachnoid space,
 wherein the CSF electrode is a subarachnoid electrode, configured to be implanted in the subarachnoid space, and
 wherein the control circuitry is configured to clear the substance from the subarachnoid space to the superior sagittal sinus.

Inventive concept 31. The apparatus according to inventive concept 24, wherein the control circuitry is configured to clear the substance by electroosmotically driving fluid from the CSF-filled space of the brain to the superior sagittal sinus.

Inventive concept 32. The apparatus according to inventive concept 31, wherein the control circuitry is configured to drive the fluid from the CSF-filled space of the brain to the superior sagittal sinus by configuring the midplane treatment electrode as a cathode, and the CSF electrode as an anode.

Inventive concept 33. The apparatus according to inventive concept 24, wherein the control circuitry is configured to clear the substance by electrophoretically driving the substance from the CSF-filled space of the brain to the superior sagittal sinus.

Inventive concept 34. The apparatus according to inventive concept 24, wherein the control circuitry is configured to apply the treatment current as direct current.

Inventive concept 35. The apparatus according to inventive concept 24, wherein the control circuitry is configured to simultaneously drive (a) the parenchymal and the CSF electrodes to clear the substance from the brain parenchyma into the CSF-filled space of the brain, and (b) apply the treatment current between the midplane treatment electrode and the CSF electrode to clear the substance from the CSF-filled space to the superior sagittal sinus.

Inventive concept 36. The apparatus according to inventive concept 35, wherein the control circuitry is configured to apply first, second, and third voltages to the parenchymal electrode, the CSF electrode, and the midplane treatment electrode, respectively, the third voltage more positive than the second voltage, which is in turn more positive than first voltage.

Inventive concept 37. The apparatus according to inventive concept 24, wherein the control circuitry is configured to alternatingly (a) drive the parenchymal and the CSF electrodes to clear the substance from the brain parenchyma into the CSF-filled space of the brain, and (b) apply the treatment current between the midplane treatment electrode and the CSF electrode to clear the substance from the CSF-filled space to the superior sagittal sinus.

Inventive concept 38. The apparatus according to any one of inventive concepts 1-2, wherein the cerebrospinal fluid (CSF) electrode is a first a cerebrospinal fluid (CSF) electrode, wherein the apparatus further comprises:

a midplane treatment electrode, adapted to be disposed in or over a superior sagittal sinus; and a second cerebrospinal fluid (CSF) electrode, configured to be implanted in a CSF-filled space of a brain of the subject, the CSF-filled space selected from the group consisting of: a ventricular system and a subarachnoid space, and wherein the control circuitry is configured to clear the substance from the CSF-filled space of the brain to the superior sagittal sinus, by applying a treatment current between (a) the midplane treatment electrode and (b) the second CSF electrode.

Inventive concept 39. The apparatus according to inventive concept 38, wherein the midplane treatment electrode is adapted to be disposed over the superior sagittal sinus.

Inventive concept 40. The apparatus according to inventive concept 39, wherein the midplane treatment electrode is adapted to be disposed over the superior sagittal sinus, outside and in electrical contact with a skull of a head of the subject.

Inventive concept 41. The apparatus according to inventive concept 39, wherein the midplane treatment electrode is adapted to be disposed over the superior sagittal sinus, under a skull of a head of the subject.

Inventive concept 42. The apparatus according to inventive concept 38, wherein the midplane treatment electrode is adapted to be implanted in the superior sagittal sinus.

Inventive concept 43. The apparatus according to any one of inventive concepts 1-2, further comprising:

midplane treatment electrodes, adapted to be disposed over a superior sagittal sinus; and lateral treatment electrodes, adapted to be disposed between 1 and 12 cm of a sagittal midplane of a skull of a head of the subject, wherein the control circuitry is configured to clear the substance from the subarachnoid space to the superior sagittal sinus, by applying one or more treatment currents between (a) one or more of the midplane treatment electrodes and (b) one or more of the lateral treatment electrodes.

Inventive concept 44. The apparatus according to inventive concept 43, wherein the midplane treatment electrodes are adapted to be disposed over the superior sagittal sinus, outside and in electrical contact with a skull of a head of the subject.

Inventive concept 45. The apparatus according to inventive concept 43, wherein the midplane treatment electrodes are adapted to be disposed over the superior sagittal sinus, under a skull of a head of the subject.

Inventive concept 46. The apparatus according to inventive concept 43, wherein the control circuitry is configured to clear the substance by electroosmotically driving fluid from the subarachnoid space to the superior sagittal sinus.

Inventive concept 47. The apparatus according to inventive concept 46, wherein the control circuitry is configured to configure the midplane treatment electrodes as cathodes, and the lateral treatment electrodes as anodes.

Inventive concept 48. The apparatus according to inventive concept 46, wherein the lateral treatment electrodes comprise (a) left lateral treatment electrodes, which are adapted to be disposed left of the sagittal midplane of the skull, and (b) right lateral treatment electrodes, which are adapted to be disposed right of the sagittal midplane of the skull, and wherein the control circuitry is configured to configure the midplane treatment electrodes as cathodes, and the left and the right lateral treatment electrodes as left and right anodes, respectively.

Inventive concept 49. The apparatus according to inventive concept 43, wherein the control circuitry is configured to clear the substance by electrophoretically driving the substance from the subarachnoid space to the superior sagittal sinus.

Inventive concept 50. The apparatus according to inventive concept 49, wherein the lateral treatment electrodes comprise (a) left lateral treatment electrodes, which are adapted to be disposed left of the sagittal midplane of the skull, and (b) right lateral treatment electrodes, which are adapted to be disposed right of the sagittal midplane of the skull, and wherein the control circuitry is configured to configure the midplane treatment electrodes as anodes, and the left and the right lateral treatment electrodes as left and right cathodes, respectively.

Inventive concept 51. The apparatus according to inventive concept 43, wherein the lateral treatment electrodes are adapted to be implanted under an arachnoid mater of the subject.

Inventive concept 52. The apparatus according to inventive concept 51, wherein the lateral treatment electrodes are adapted to be disposed in the subarachnoid space.

Inventive concept 53. The apparatus according to inventive concept 51, wherein the lateral treatment electrodes are adapted to be disposed in gray or white matter of a brain of the subject.

Inventive concept 54. The apparatus according to inventive concept 43, wherein the control circuitry is configured to apply the one or more treatment currents as direct currents.

There is still further provided, in accordance with an inventive concept 55 of the present invention, a method comprising:

implanting a parenchymal electrode in electrical contact with brain parenchyma of a subject identified as at risk of or suffering from a disease;

implanting a cerebrospinal fluid (CSF) electrode in a CSF-filled space of a brain of the subject, the CSF-filled space selected from the group consisting of: a ventricular system and a subarachnoid space; and activating control circuitry to drive the parenchymal and the CSF electrodes to clear a substance from the brain parenchyma into the CSF-filled space of the brain.

Inventive concept 56. The method according to inventive concept 55, wherein the disease is Alzheimer's disease, and wherein implanting parenchymal electrode comprises implanting the parenchymal electrode in the subject identified as at risk of or suffering from Alzheimer's disease.

Inventive concept 57. The method according to inventive concept 55, wherein the disease is cerebral amyloid angiopathy (CAA), and wherein implanting parenchymal electrode comprises implanting the parenchymal electrode in the subject identified as at risk of or suffering from CAA.

Inventive concept 58. The method according to inventive concept 55, wherein the CSF-filled space of the brain is the ventricular system, wherein the CSF electrode is a ventricular electrode, and wherein activating the control circuitry comprises activating the control circuitry to drive the parenchymal and the ventricular electrodes to clear the substance from the brain parenchyma into the ventricular system.

Inventive concept 59. The method according to inventive concept 55, wherein the CSF-filled space of the brain is the subarachnoid space, wherein the CSF electrode is a subarachnoid electrode, and wherein activating the control circuitry comprises activating the control circuitry to drive the parenchymal and the subarachnoid electrodes to clear the substance from the brain parenchyma into the subarachnoid space.

Inventive concept 60. The method according to inventive concept 55, wherein the substance includes amyloid beta, and wherein activating the control circuitry comprises activating the control circuitry to drive the parenchymal and the CSF electrodes to clear the amyloid beta from the brain parenchyma into the CSF-filled space of the brain.

Inventive concept 61. The method according to inventive concept 55, wherein the substance includes metal ions, and wherein activating the control circuitry comprises activating the control circuitry to drive the parenchymal and the CSF electrodes to clear the metal ions from the brain parenchyma into the CSF-filled space of the brain.

Inventive concept 62. The method according to inventive concept 55, wherein the substance includes tau protein, and wherein activating the control circuitry comprises activating the control circuitry to drive the parenchymal and the CSF electrodes to clear the tau protein from the brain parenchyma into the CSF-filled space of the brain.

Inventive concept 63. The method according to inventive concept 55, wherein implanting the parenchymal electrode in electrical contact with the brain parenchyma comprises implanting the parenchymal electrode in the brain parenchyma.

Inventive concept 64. The method according to inventive concept 63, wherein implanting the parenchymal electrode in the brain parenchyma comprises implanting the parenchymal electrode in white matter of the brain.

Inventive concept 65. The method according to inventive concept 63, wherein implanting the parenchymal and the CSF electrodes comprises implanting the parenchymal and the CSF electrodes such that an area of build-up of the substance is between the parenchymal and the CSF electrodes.

Inventive concept 66. The method according to inventive concept 65, wherein implanting the parenchymal and the CSF electrodes comprises identifying the area of build-up of the substance in the brain parenchyma before implanting the parenchymal and the CSF electrodes.

Inventive concept 67. The method according to inventive concept 66, wherein identifying the area of build-up comprises performing imaging of the brain.

Inventive concept 68. The method according to inventive concept 67, wherein performing the imaging comprises performing functional MRI (fMRI) imaging of the brain.

Inventive concept 69. The method according to inventive concept 63, wherein implanting the parenchymal electrode comprises implanting the parenchymal electrode such that an area of build-up of the substance is between the parenchymal electrode and an area of the CSF-filled space of the brain nearest the area of build-up.

Inventive concept 70. The method according to inventive concept 69, wherein implanting the parenchymal electrode comprises identifying the area of build-up of the substance in the brain parenchyma before implanting the parenchymal electrode.

Inventive concept 71. The method according to inventive concept 70, wherein identifying the area of build-up comprises performing imaging of the brain.

Inventive concept 72. The method according to inventive concept 71, wherein performing the imaging comprises performing functional MRI (fMRI) imaging of the brain.

Inventive concept 73. The method according to inventive concept 55, wherein activating the control circuitry comprises activating the control circuitry to configure the parenchymal electrode to be an anode, and the CSF electrode to be a cathode.

Inventive concept 74. The method according to inventive concept 55, wherein activating the control circuitry comprises activating the control circuitry to configure the parenchymal electrode to be a cathode, and the CSF electrode to be an anode.

Inventive concept 75. The method according to inventive concept 55, further comprising applying deep brain stimulation using the parenchymal electrode.

Inventive concept 76. The method according to inventive concept 55, further comprising implanting the control circuitry under skin of the subject.

Inventive concept 77. The method according to inventive concept 55, wherein activating the control circuitry to drive the parenchymal and the CSF electrodes comprises activating the control circuitry to drive the parenchymal and the CSF electrodes to clear the substance by applying a non-excitatory current between the parenchymal and the CSF electrodes.

Inventive concept 78. The method according to inventive concept 55, wherein activating the control circuitry to drive the parenchymal and the CSF electrodes comprises activating the control circuitry to drive the parenchymal and the CSF electrodes to clear the substance by applying direct current between the parenchymal and the CSF electrodes.

Inventive concept 79. The method according to inventive concept 78, wherein activating the control circuitry to apply the direct current comprises activating the control circuitry to apply the direct current with an average amplitude of between 1 and 5 mA.

Inventive concept 80. The method according to inventive concept 78, wherein activating the control circuitry to apply the direct current comprises activating the control circuitry to apply the direct current with an average amplitude of less than 1.2 V.

Inventive concept 81. The method according to inventive concept 78, wherein activating the control circuitry to apply the direct current comprises activating the control circuitry to apply the direct current as a series of pulses.

Inventive concept 82. The method according to inventive concept 81, wherein activating the control circuitry to apply the direct current as the series of pulses comprises activating the control circuitry to apply the direct current as the series of pulses having an average pulse duration of between 100 milliseconds and 300 seconds.

Inventive concept 83. The method according to inventive concept 81, wherein activating the control circuitry to apply the direct current as the series of pulses comprises activating the control circuitry to apply the direct current as the series of pulses with a duty cycle of between 1% and 50%.

Inventive concept 84. The method according to inventive concept 81, wherein activating the control circuitry to drive the parenchymal and the CSF electrodes comprises activating the control unit to:

drive the parenchymal and the CSF electrodes to clear the substance by applying a voltage between the parenchymal and the CSF electrodes during each of the pulses, while applying the voltage, measure a current resulting from application of the voltage during the pulse, and terminate the pulse upon the measured current falling below a threshold value.

Inventive concept 85. The method according to inventive concept 84, wherein the threshold value is based on an initial current magnitude measured upon commencement of the pulse.

Inventive concept 86. The method according to inventive concept 55,
further comprising disposing a midplane treatment electrode in or over a superior sagittal sinus,
wherein activating the control circuitry comprises activating the control circuitry to clear the substance from the CSF-filled space of the brain to the superior sagittal sinus, by applying a treatment current between the midplane treatment electrode and the CSF electrode.

Inventive concept 87. The method according to inventive concept 86, wherein disposing the midplane treatment electrode comprises disposing the midplane treatment electrode over the superior sagittal sinus.

Inventive concept 88. The method according to inventive concept 87, wherein disposing the midplane treatment electrode comprises disposing the midplane treatment electrode over the superior sagittal sinus, outside and in electrical contact with a skull of a head of the subject.

Inventive concept 89. The method according to inventive concept 87, wherein disposing the midplane treatment electrode comprises disposing the midplane treatment electrode over the superior sagittal sinus, under a skull of a head of the subject.

Inventive concept 90. The method according to inventive concept 86, wherein disposing the midplane treatment electrode comprises implanting the midplane treatment electrode in the superior sagittal sinus.

Inventive concept 91. The method according to inventive concept 86, wherein implanting the CSF electrode comprises implanting the CSF electrode between 1 and 12 cm of a sagittal midplane of a skull of the subject.

Inventive concept 92. The method according to inventive concept 86,
wherein the CSF-filled space of the brain is the subarachnoid space,
wherein the CSF electrode is a subarachnoid electrode, and
wherein activating the control circuitry comprises activating the control circuitry to clear the substance from the subarachnoid space to the superior sagittal sinus.

Inventive concept 93. The method according to inventive concept 86, wherein activating the control circuitry comprises activating the control circuitry to clear the substance by electroosmotically driving fluid from the CSF-filled space of the brain to the superior sagittal sinus.

Inventive concept 94. The method according to inventive concept 93, wherein activating the control circuitry comprises activating the control circuitry to drive the fluid from the CSF-filled space of the brain to the superior sagittal sinus by configuring the midplane treatment electrode as a cathode, and the CSF electrode as an anode.

Inventive concept 95. The method according to inventive concept 86, wherein activating the control circuitry comprises activating the control circuitry to clear the substance by electrophoretically driving the substance from the CSF-filled space of the brain to the superior sagittal sinus.

Inventive concept 96. The method according to inventive concept 86, wherein activating the control circuitry comprises activating the control circuitry to apply the treatment current as direct current.

Inventive concept 97. The method according to inventive concept 86, wherein activating the control circuitry comprises activating the control circuitry to simultaneously drive (a) the parenchymal and the CSF electrodes to clear the substance from the brain parenchyma into the CSF-filled space of the brain, and (b) apply the treatment current between the midplane treatment electrode and the CSF electrode to clear the substance from the CSF-filled space to the superior sagittal sinus.

Inventive concept 98. The method according to inventive concept 97, wherein activating the control circuitry comprises activating the control circuitry to apply first, second, and third voltages to the parenchymal electrode, the CSF electrode, and the midplane treatment electrode, respectively, the third voltage more positive than the second voltage, which is in turn more positive than first voltage.

Inventive concept 99. The method according to inventive concept 86, wherein activating the control circuitry comprises activating the control circuitry to alternatingly (a) drive the parenchymal and the CSF electrodes to clear the substance from the brain parenchyma into the CSF-filled space of the brain, and (b) apply the treatment current between the midplane treatment electrode and the CSF electrode to clear the substance from the CSF-filled space to the superior sagittal sinus.

Inventive concept 100. The method according to inventive concept 55,
wherein the cerebrospinal fluid (CSF) electrode is a first a cerebrospinal fluid (CSF) electrode,
wherein the method further comprises:
disposing a midplane treatment electrode in or over a superior sagittal sinus; and
implanting a second cerebrospinal fluid (CSF) electrode in a CSF-filled space of a brain of the subject, the CSF-filled space selected from the group consisting of: a ventricular system and a subarachnoid space, and
wherein activating the control circuitry comprises activating the control circuitry to clear the substance from the CSF-filled space of the brain to the superior sagittal sinus, by applying a treatment current between (a) the midplane treatment electrode and (b) the second CSF electrode.

Inventive concept 101. The method according to inventive concept 100, wherein disposing the midplane treatment electrode comprises disposing the midplane treatment electrode over the superior sagittal sinus.

Inventive concept 102. The method according to inventive concept 101, wherein disposing the midplane treatment electrode comprises disposing the midplane treatment electrode over the superior sagittal sinus, outside and in electrical contact with a skull of a head of the subject.

Inventive concept 103. The method according to inventive concept 101, wherein disposing the midplane treatment electrode comprises disposing the midplane treatment electrode over the superior sagittal sinus, under a skull of a head of the subject.

Inventive concept 104. The method according to inventive concept 100, wherein disposing the midplane treatment electrode comprises implanting the midplane treatment electrode in the superior sagittal sinus.

Inventive concept 105. The method according to inventive concept 55, further comprising:
disposing midplane treatment electrodes over a superior sagittal sinus; and
disposing lateral treatment electrodes between 1 and 12 cm of a sagittal midplane of a skull of a head of the subject,
wherein activating the control circuitry comprises activating the control circuitry to clear the substance from the subarachnoid space to the superior sagittal sinus, by applying one or more treatment currents between (a) one or more of the midplane treatment electrodes and (b) one or more of the lateral treatment electrodes.

Inventive concept 106. The method according to inventive concept 105, wherein disposing the midplane treatment electrodes comprises disposing the midplane treatment electrodes over the superior sagittal sinus, outside and in electrical contact with a skull of a head of the subject.

Inventive concept 107. The method according to inventive concept 105, wherein disposing the midplane treatment electrodes comprises disposing the midplane treatment electrodes over the superior sagittal sinus, under a skull of a head of the subject.

Inventive concept 108. The method according to inventive concept 105, wherein activating the control circuitry comprises activating the control circuitry to clear the substance by electroosmotically driving fluid from the subarachnoid space to the superior sagittal sinus.

Inventive concept 109. The method according to inventive concept 108, wherein activating the control circuitry comprises activating the control circuitry to configure the midplane treatment electrodes as cathodes, and the lateral treatment electrodes as anodes.

Inventive concept 110. The method according to inventive concept 108, wherein the lateral treatment electrodes include left lateral treatment electrodes and right lateral treatment electrodes, wherein disposing the lateral treatment electrodes includes disposing the left lateral treatment electrodes left of the sagittal midplane of the skull, and disposing the right lateral treatment electrodes right of the sagittal midplane of the skull, and wherein activating the control circuitry includes activating the control circuitry to configure the midplane treatment electrodes as cathodes, and the left and the right lateral treatment electrodes as left and right anodes, respectively.

Inventive concept 111. The method according to inventive concept 105, wherein activating the control circuitry comprises activating the control circuitry to clear the substance by electrophoretically driving the substance from the subarachnoid space to the superior sagittal sinus.

Inventive concept 112. The method according to inventive concept 111, wherein the lateral treatment electrodes include left lateral treatment electrodes and right lateral treatment electrodes, wherein disposing the lateral treatment electrodes includes disposing the left lateral treatment electrodes left of the sagittal midplane of the skull, and disposing the right lateral treatment electrodes right of the sagittal midplane of the skull, and wherein activating the control circuitry includes activating the control circuitry to configure the midplane treatment electrodes as anodes, and the left and the right lateral treatment electrodes as left and right cathodes, respectively.

Inventive concept 113. The method according to inventive concept 105, wherein disposing the lateral treatment electrodes comprises implanting the lateral treatment electrodes under an arachnoid mater of the subject.

Inventive concept 114. The method according to inventive concept 113, wherein disposing the lateral treatment electrodes comprises disposing the lateral treatment electrodes in the subarachnoid space.

Inventive concept 115. The method according to inventive concept 113, wherein disposing the lateral treatment electrodes comprises disposing the lateral treatment electrodes in gray or white matter of a brain of the subject.

Inventive concept 116. The method according to inventive concept 105, wherein activating the control circuitry comprises activating the control circuitry to apply the one or more treatment currents as direct currents.

The present invention will be more fully understood from the following detailed description of embodiments thereof, taken together with the drawings, in which:

DETAILED DESCRIPTION OF APPLICATIONS

Figure 1A:
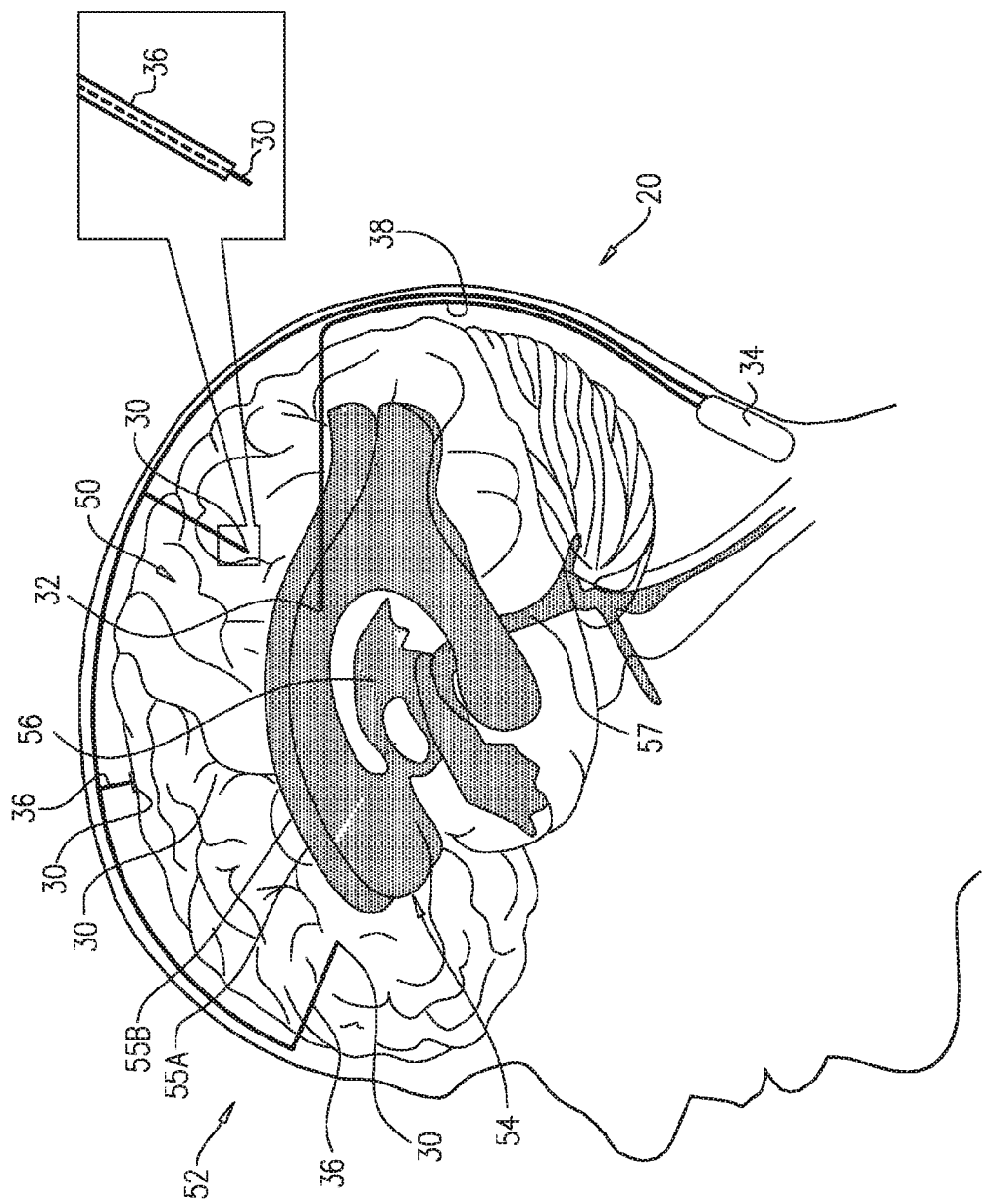
FIGS. 1A-C are schematic illustrations of a system for treating Alzheimer's disease, in accordance with respective applications of the present invention.
Figure 1B:
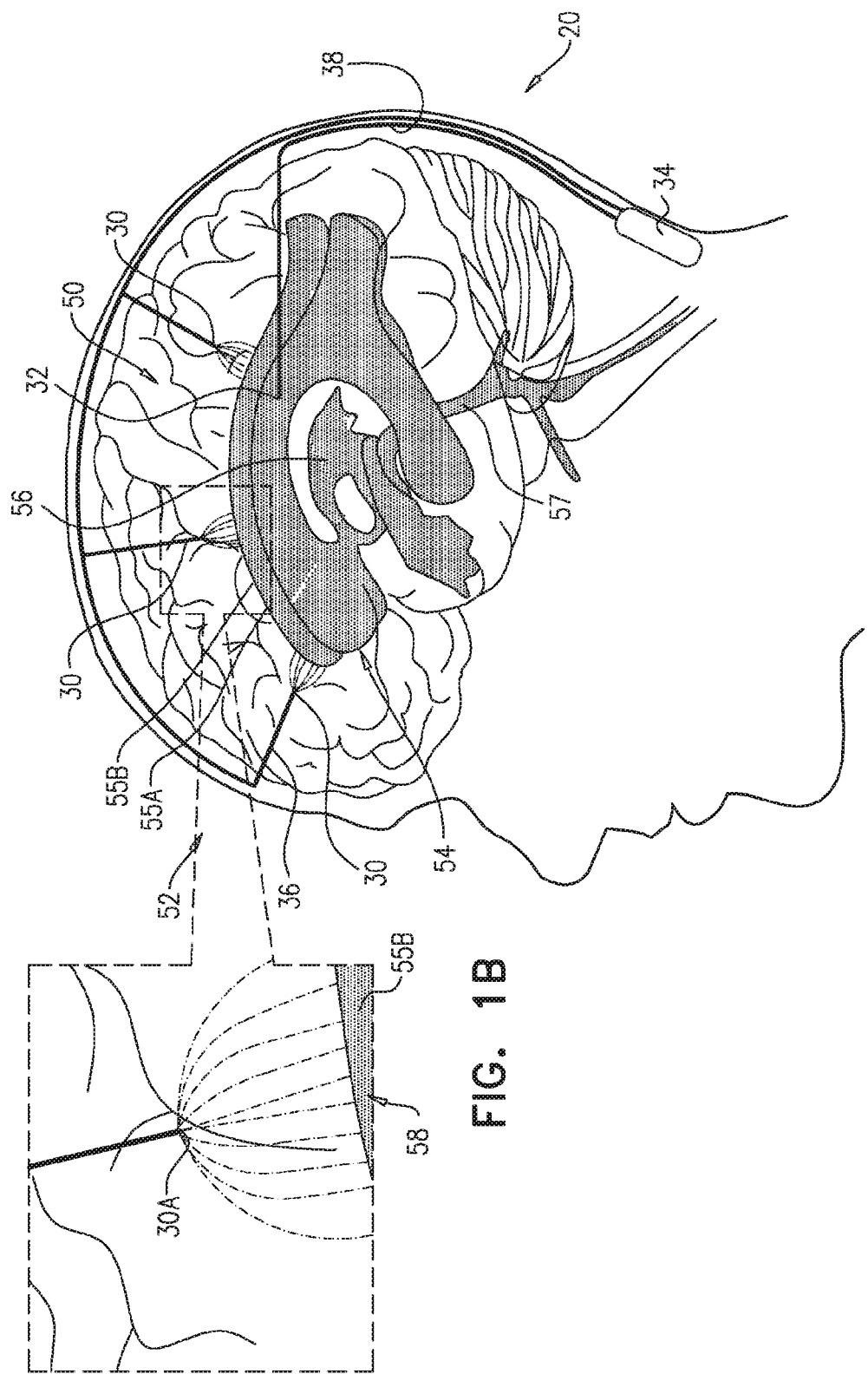
Figure 1C:
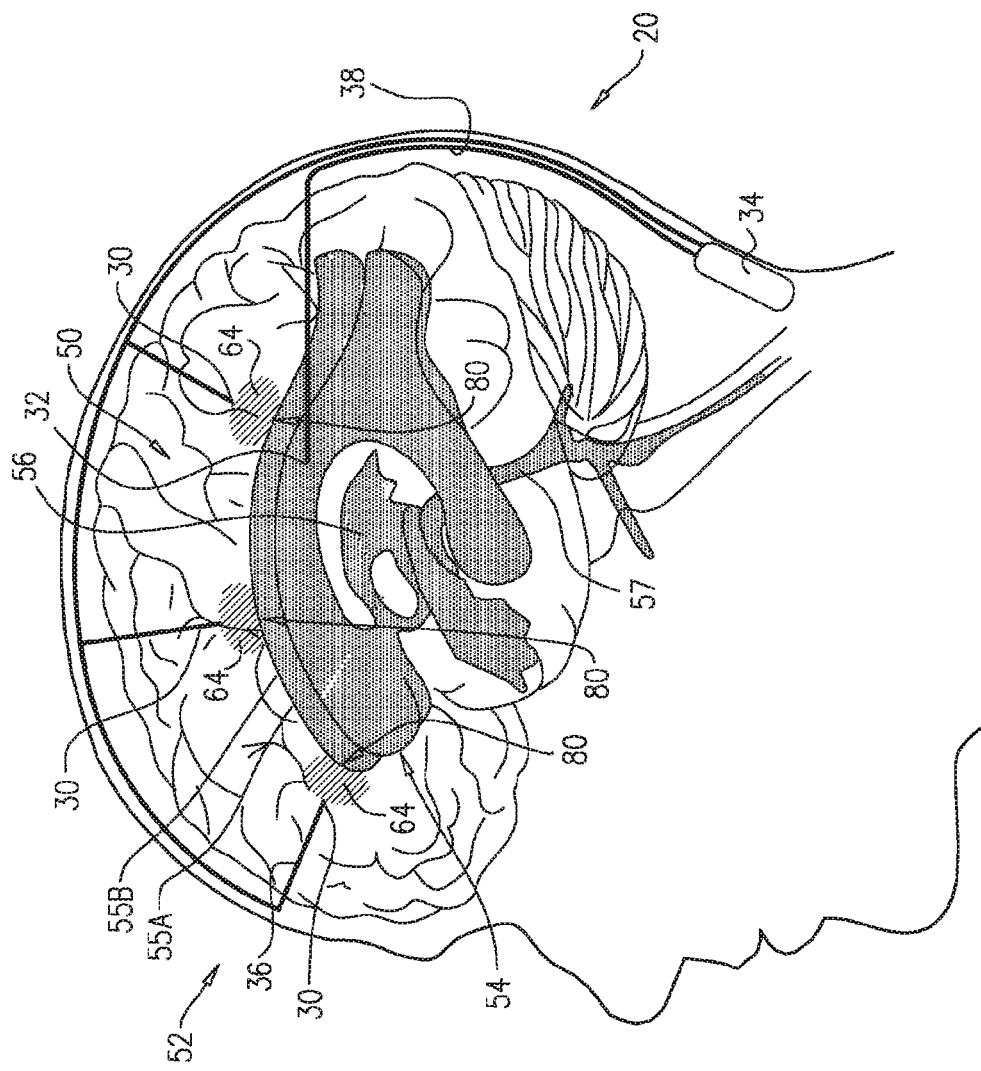

FIGS. 1A-C are schematic illustrations of a system 20 for treating Alzheimer's disease and/or cerebral amyloid angiopathy (CAA), in accordance with respective applications of the present invention. System 20 comprises parenchymal and cerebrospinal fluid (CSF) electrodes 30 and 32, and control circuitry 34, which is electrically coupled to parenchymal and CSF electrodes 30 and 32, typically by parenchymal and CSF electrode leads 36 and 38, respectively.

In some applications of the present invention, as shown for two of parenchymal electrodes 30 illustrated in FIG. 1A, parenchymal electrode 30 is implanted in parenchyma 50 of a brain 52 of a subject identified as at risk of or suffering from Alzheimer's disease and/or from CAA, e.g., using surgical techniques similar to those used for implantation of electrodes for deep brain stimulation. Alternatively, parenchymal electrode 30 is implanted elsewhere in the subject in electrical contact with brain parenchyma 50, such as on and in contact with an outer surface of brain 52, as shown for the middle parenchymal electrode 30 illustrated in FIG. 1A. CSF electrode 32 is implanted in a CSF-filled space of the brain, such as ventricular system 54 of brain 52 or a subarachnoid space 144 (labeled in FIGS. 4A-G) (e.g., cisterns of subarachnoid space 144). For example, CSF electrode 32 may be implanted using techniques known for implanting hydrocephalus shunts, mutatis mutandis. As used in the present application, including in the claims, ventricular system 54 includes and is limited to lateral ventricles 55 (left and right lateral ventricles 55A and 55B), a third ventricle 56, a fourth ventricle 57, a cerebral aqueduct 59 (labeled in FIGS. 4A-G), interventricular foramina, a median aperture, and left and right lateral apertures.

Control circuitry 34 is activated to drive parenchymal and CSF electrodes 30 and 32 to clear a substance from brain parenchyma 50 into the CSF-filled space, such as ventricular system 54. For some applications, the substance comprises amyloid beta, metal ions, a tau protein, and/or a waste substance. As used in the present application, including in the claims, clearing a substance from the brain parenchyma is to be understood as including clearing a portion of the substance, without clearing all of the substance. Typically, in order to clear the substance, control circuitry 34 applies a voltage or a current between parenchymal and CSF electrodes 30 and 32 (i.e., control circuitry 34 regulates the voltage or the current).

Typically, a healthcare worker, such as a physician, activates control circuitry 34 to provide the functions described herein. Activating the control unit may include configuring parameters and/or functions of the control circuitry (such as using a separate programmer or external controller), or activating the control unit to perform functions preprogrammed in the control circuitry. Control circuitry 34 typically comprises appropriate memory, processor(s), and hardware running software that is configured to provide the functionality of control circuitry described herein.

Current may flow generally through tissue that is located between parenchymal and CSF electrodes 30 and 32. Alternatively or additionally, at least a portion of the current may flow between (a) parenchymal electrode 30 and (b) an area of the CSF-filled space (e.g., ventricular system 54) nearest parenchymal electrode 30. The inventors have appreciated that because of the low electrical resistance of cerebrospinal fluid (CSF) in the CSF-filled space, such as ventricular system 54, the ventricles are to some extent a single entity electrically. Therefore, a large portion of the current flows to the nearest portion of ventricular system 54, even if CSF electrode 32 is implanted in a ventricle remote from parenchymal electrode 30. For example, as shown in FIG. 1B, if a parenchymal electrode 30A is implanted in a right hemisphere of brain 52, most of the current may flow between parenchymal electrode 30A and an area 58 of right ventricle 55B nearest parenchymal electrode 30A, even though CSF electrode 32 is implanted in left ventricle 55A.

For some applications, the voltage applied between the electrodes may clear the substance electrophoretically, because of a positive or negative charged interface between the surface of the particles of the substance and the surrounding brain tissue fluids. For these applications, the voltage applied between the electrodes causes a potential difference between brain parenchyma 50 and the CSF-filled space, such as ventricular system 54, which causes movement of the substance from brain parenchyma 50 to the CSF-filled space, such as ventricular system 54. Alternatively or additionally, for some applications, the voltage applied between the electrodes may clear the substance electroosmotically, because of a positive or negative charge of fluid in the parenchyma. For these applications, the voltage applied between the electrodes causes a potential difference between brain parenchyma 50 and the CSF-filled space, such as ventricular system 54, which causes increased flow from brain parenchyma 50 to the CSF-filled space, such as ventricular system 54, and thus increased transport of the substance from parenchyma 50 to the CSF-filled space, such as ventricular system 54.

For some applications, system 20 comprises a plurality of parenchymal electrodes 30 and/or a plurality of CSF electrodes 32. Parenchymal electrodes 30 may be implanted in one or both hemispheres of brain 52, and/or at one or more than one location in each of the hemispheres. For some applications, such as shown in FIGS. 1A-C, system 20 comprises a plurality of parenchymal electrodes 30 and exactly one CSF electrode 32. For example, the single CSF electrode 32 may be implanted in one of lateral ventricles 55 or third ventricle 56, which, as discussed above, are to a large degree in good electrical connectivity with the other ventricles. For other applications (configuration not shown), system 20 comprises (a) exactly two CSF electrodes 32, which are implanted in left and right lateral ventricles 55A and 55B, respectively, or (b) exactly three CSF electrodes 32, which are implanted in left and right lateral ventricles 55A and 55B and third ventricle 56, respectively.

For applications in which system 20 comprises a plurality of parenchymal electrodes 30 and/or a plurality of CSF electrodes 32, system 20 typically comprises a corresponding plurality of parenchymal electrode leads 36 and/or a corresponding plurality of CSF electrode leads 38. Each of the leads may comprise separate electrical insulation, and/or a portion of the leads may be joined and share common electrical insulation, as shown in FIGS. 1A-C for parenchymal electrode leads 36. Control circuitry 34 may be activated to independently drive parenchymal electrodes 30, e.g., using separately circuitry. Alternatively, one or more of parenchymal electrodes 30 may be shorted to one another, such that the control circuitry drives the shorted electrodes together. Control circuitry 34 may be activated to drive parenchymal electrodes 30 simultaneously or at different times.

For some applications, brain parenchyma 50 in which parenchymal electrode 30 is implanted comprises white matter of the brain.

As used in the present application, including the claims, "treating" includes both treating a subject already diagnosed with Alzheimer's disease and/or CAA (such as by delaying, slowing, or reversing progression of the disease, e.g., in a patient diagnosed at an early stage), as well as preventing the development of Alzheimer's disease and/or CAA in a subject not diagnosed with the disease and/or asymptomatic for the disease. For example, the techniques described herein may be used to prevent or delay the development of Alzheimer's disease and/or CAA in responsive to detection of an abnormal level of amyloid beta, such as using a blood test or a spinal tap.

For some applications, control circuitry 34 is configured to be implanted subcutaneously, such under skin of the skull of the subject if the housing containing the control circuitry is small, or elsewhere in the subject's body, such as in the upper chest, if the housing of the control circuitry is larger (e.g., includes batteries), with leads through the neck, or optionally in the head. For these applications, control circuitry 34 is typically driven by an external controller that is in wireless or wired communication with control circuitry 34. For some applications, the external controller is mounted on a bed of the subject (e.g., disposed within a mattress), and is configured to activate control circuitry 34 only at night, and/or only when the subject is sleeping. Such nighttime activation may to some degree mimic the natural timing of clearance of the substance (e.g., amyloid beta or tau protein) during sleep, during which the extracellular spaces are wider than during wakefulness, which allows more interstitial fluid (ISF) flow within the brain. For other applications, control circuitry 34 is configured to be disposed externally to the subject.

For some applications, control circuitry 34 is activated to drive parenchymal and CSF electrodes 30 and 32 to clear the substance by applying a non-excitatory current between parenchymal and CSF electrodes 30 and 32, i.e., the current does not cause propagation of action potentials. Thus, in these applications, control circuitry 34 is activated to set parameters of the current such that the current does not affect, or only minimally affects, neuronal activity. Alternatively, the applied current does excite brain tissue, such as to a small extent.

For some applications, control circuitry 34 is activated to drive parenchymal and CSF electrodes 30 and 32 to clear the substance by applying direct current (DC) between parenchymal and CSF electrodes 30 and 32. As used in the present application, including in the claims, direct current means a current having a constant polarity; the amplitude of the direct current may or may not vary over time, and may sometimes be zero.

For some applications, control circuitry 34 is activated to apply the direct current with an average amplitude of at least 1 mA, no more than 5 mA, and/or between 1 and 5 mA. Alternatively or additionally, for some applications, control circuitry 34 is activated to apply the direct current with an average amplitude of less than 1.2 V (such an amplitude may avoid electrolysis in the vicinity of one or both of the electrodes).

For some applications, such as when the substance is amyloid beta, control circuitry 34 is activated to configure parenchymal electrode 30 to be a cathode, and CSF electrode 32 to be an anode. Alternatively, control circuitry 34 is activated to configure parenchymal electrode 30 to be an anode, and CSF electrode 32 to be a cathode. For applications in which the voltage applied between the electrodes clears the substance electrophoretically, the selected polarity of the electrodes typically depends on whether the substance has a positive or negative effective charge. Similarly, for applications in which the voltage applied between the electrodes clears the substance electroosmotically, the selected polarity of the electrodes typically depends on whether the fluid has a positive or negative effective charge.

For some applications, control circuitry 34 is activated to apply the direct current as a series of pulses. For some applications, the series of pulses has an average pulse duration of at least 10 milliseconds, no more than 300 seconds, and/or between 10 milliseconds and 300 seconds, such as: (a) at least 10 milliseconds, no more than 100 milliseconds, and/or between 10 and 100 milliseconds, (b) at least 100 milliseconds, no more than 300 seconds (e.g., no more than 500 milliseconds), and/or between 100 and 300 seconds (e.g., between 100 and 500 milliseconds), (c) at least 500 milliseconds, no more than 5 seconds, and/or between 500 milliseconds and 5 seconds, (d) at least 5 seconds, no more than 10 seconds, and/or between 5 and 10 seconds, or (e) at least 10 seconds, no more than 100 seconds, and/or between 10 and 100 seconds. For some applications, the pulses are applied at a frequency of at least 0.001 Hz, no more than 1 kHz, and/or between 0.001 and 1 kHz, such as: (a) at least 100 Hz, no more than 1 kHz, and/or between 100 Hz and 1 kHz, (b) at least 20 Hz, no more than 100 Hz, and/or between 20 and 100 Hz, or (c) at least 1 Hz, no more than 10 Hz, and/or between 1 and 10 Hz. Alternatively or additionally, for some applications, the series of pulses has a duty cycle of at least 1%, no more than 50%, and/or between 1% and 50%, such as: (a) at least 1%, no more than 5%, and/or between 1% and 5%, (b) at least 5%, no more than 10%, and/or between 5% and 10%, (c) at least 10%, no more than 25%, and/or between 10% and 25%, or (d) at least 25%, no more than 50%, and/or between 25% and 50%. Typically, but not necessarily, the duty cycle is no more than 90%, because a given level of applied voltage produces higher current in the tissue if the capacitance in the tissue is allowed to discharge between pulses.

For some of the applications in which control circuitry 34 applies a voltage between parenchymal and CSF electrodes 30 and 32 in a series of DC pulses, the resulting current decays because of the effects of tissue electrolytes. The current may decay by about two-thirds of its initial magnitude within tens of milliseconds after commencement of application of each pulse. In order to overcome this capacitance effect, control circuitry 34 is activated to apply the voltage intermittently, in order to provide time periods between pulses during which the capacitance discharges.

For some applications, control circuitry 34 is activated to apply the voltage intermittently with a preprogrammed frequency and/or duty cycle. These parameters may be (a) applicable to all patients or a subgroup of patients, (b) set during a calibration procedure upon implantation of the electrodes, or (c) set based on a geometry of placement of parenchymal and/or CSF electrodes 30 and/or 32. Alternatively, control circuitry 34 is configured to set these parameters in real time by sensing the current resulting from the applied voltage.

For some applications, control circuitry 34 is activated to measure the current resulting from the applied voltage during each of the applied pulses, and to terminate each of the applied pulses when the magnitude of the measured current falls below a threshold value. For example, the threshold value may be a preprogrammed constant, or may be based on (e.g., a percentage of) the initial current magnitude measured upon commencement of the respective pulse. Control circuitry 34 waits during a discharge period before applying the next pulse.

For some applications, control circuitry 34 is activated to apply, between parenchymal and CSF electrodes 30 and 32, alternating current (AC) in:
- a primary subset of the pulses at a primary polarity selected to electrophoretically and/or electroosmotically clear the substance, at a primary voltage and with a primary average pulse duration, and
- a secondary subset of the pulses at a secondary polarity opposite the primary polarity, at a secondary voltage less than the primary voltage, and with a secondary average pulse duration greater than the primary average pulse duration.

Because of the lower secondary voltage, the secondary subset of the pulses to a large extent does not reverse the clearance of the substance achieved during application of the primary subset of the pulses. This technique may also help avoid electrolysis in the vicinity of one or both of the electrodes, even if the primary voltage is higher than a threshold DC voltage (e.g., 1.2 V) that might otherwise cause electrolysis.

For some applications, such as illustrated in FIG. 1C, parenchymal and CSF electrodes 30 and 32 are implanted such that one or more areas of build-up 64 of the substance in brain parenchyma 50 is between the electrodes, rather than implanting parenchymal electrode 30 within the area of build-up. For example, the area(s) of build-up may include amyloid plaque and/or tau protein-related nerve tissue tangles. To this end, typically the area of build-up is first identified, for example by performing imaging of brain 52, such as MRI (e.g., functional MRI (fMRI)) or PET imaging of brain 52. As mentioned above, a plurality of parenchymal electrodes 30 and/or a plurality of CSF electrodes 32 may be implanted, such as if there is more than one area of build-up 64 of the substance.

For some applications, also such as illustrated in FIG. 1C, the one or more parenchymal electrode are implanted such that the one or more areas of build-up 64 are between parenchymal electrode 30A and respective areas 80 of the CSF-filled space, such as ventricular system 54, nearest areas of build-up 64. CSF electrode 32 may or may not be implanted near areas 80. For applications in which CSF electrode 32 is not implanted near areas 80, the substance of area of build-up 64 may still be driven into nearest areas 80 of the CSF-filled space, such as ventricular system 54, because nearest areas 80 are in fluid communication with CSF electrode 32 via CSF of the CSF-filled space, such as ventricular system 54, as discussed above. As mentioned above, a plurality of parenchymal electrodes 30 and/or a plurality of CSF electrodes 32 may be implanted, such as if there is more than one area of build-up 64 of the substance, or in general in order to provide good clearance of the substance.

For some applications, parenchymal electrode 30 is further used for applying deep brain stimulation, as is known in the art. For example, the deep brain stimulation may be applied when the electrodes are not being driven to drive the substance into the CSF-filled space, such as the ventricular system. As is known in the art, the deep brain stimulation may be applied to reduce tremor and block involuntary movements in patients with motion disorders, such as Parkinson's disease, or to treat epilepsy, cluster headaches, Tourette syndrome, chronic pain, or major depression. The implantation location of parenchymal electrode 30 may be selected to be appropriate for the treatment of a particular condition, as well as for clearing the substance.

For some applications, control circuitry 34 is activated to drive parenchymal and CSF electrodes 30 and 32 in sessions, each of which has a duration of several seconds or several minutes, or continuously for longer periods (e.g., 30 minutes). For some applications, the electrodes are not driven for a period that is at least an hour. Optionally, control circuitry 34 is activated to drive the electrodes only when the subject is sleeping, such as to take advantage of the widening of extracellular spaces and/or to inhibit any sensations that may be associated with the driving. For example, control circuitry 34 may be activated to use one or more of the electrodes as EEG electrodes to detect sleep. For some applications, power for activating and/or charging control circuitry 34 is transmitted from a wireless energy transmitter in a device applied to the head, such as a hat, or from a wireless energy transmitter in, under, or above a mattress, such as described hereinabove. For some applications, control circuitry 34 is activated to drive the electrodes according to a pre-selected schedule, such as a duty cycle, such as for a few hours per day. For example, control circuitry 34 may be configured to be controlled and/or powered by an extracorporeal control circuitry, such as a control circuitry comprising a wireless transmitter, disposed in and/or in the vicinity of the subject's bed. For some applications, one or more rest periods during which the control circuitry does not drive the electrodes are provided in the pre-selected schedule.

For any of the applications described herein, CSF electrode 32 may be implanted in one of the following sites, rather than in ventricular system 54:
  a central canal of the spinal cord (which is in fluid communication with ventricular system 54); or
  a subarachnoid space 144 (labeled in FIGS. 4A-G) (which is in fluid communication with ventricular system 54 because CSF drains into cisterns of subarachnoid space 144 via foramina of ventricular system 54).

For some applications, instead of implanting CSF electrode 32 in ventricular system 54, an electrode is implanted in superior sagittal sinus 142 (labeled in FIGS. 4A-G).

For any of the applications described herein, parenchymal electrode 30 may be implanted in superior sagittal sinus 142, rather than in brain parenchyma 50 (typically, in these applications, CSF electrode 32 is implanted in ventricular system 54).

Reference is again made to FIGS. 1A-C. For some applications, control circuitry 34 is configured to detect a voltage difference between parenchyma 50 and the CSF-filled space, and set a level of the voltage applied between parenchymal and cerebrospinal fluid (CSF) electrodes 30 and 32 responsively to the detected voltage difference.

Figure 2A:
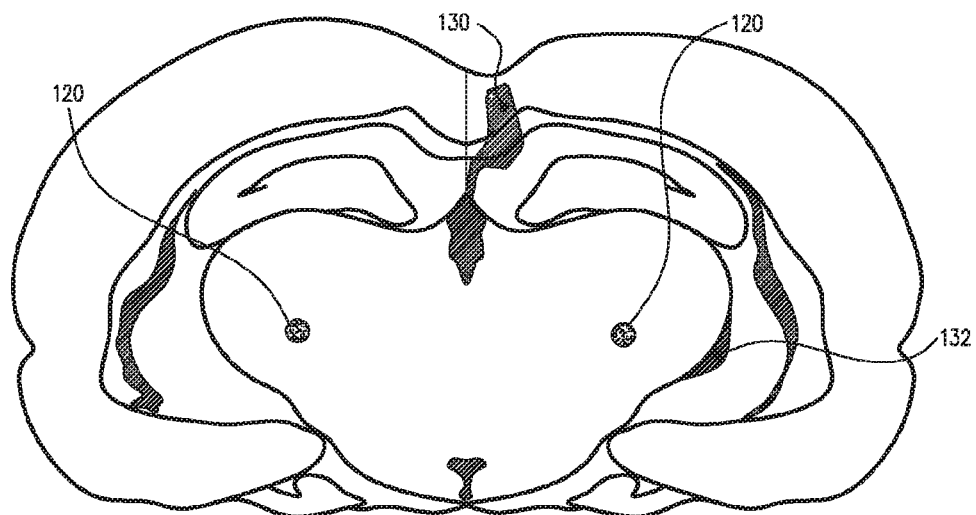
FIGS. 2A-B are schematic illustrations of cross-sections of a rat brain showing results of an animal experiment performed in accordance with an application of the present invention.
Figure 2B:
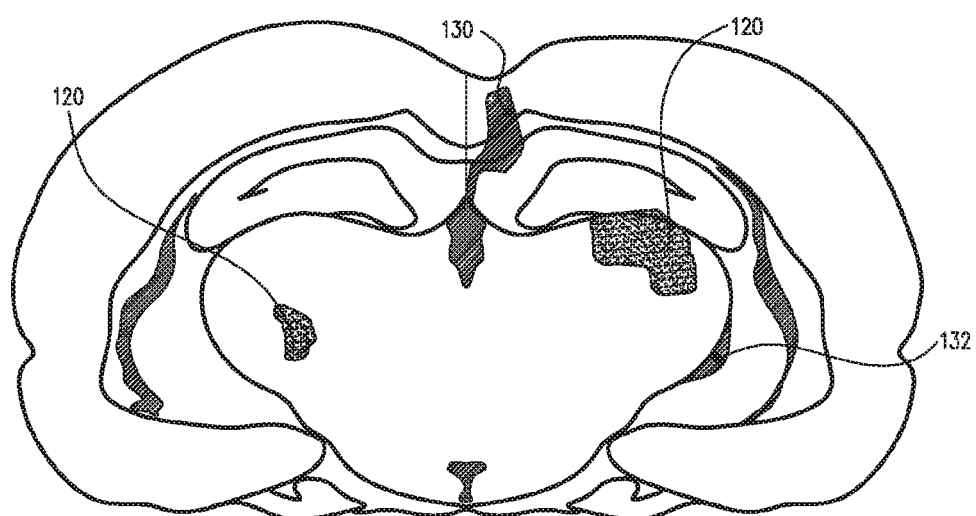

Reference is now made to FIGS. 2A-B, which are schematic illustrations of cross-sections of a rat brain showing results of an animal experiment performed in accordance with an application of the present invention. A rat was anesthetized, a first electrode 130 (a piece of Pt—Ir wire soldered to a miniature connector) was inserted through a hole into the sagittal sinus, and a second electrode 132 (a pieces of Pt—Ir wire soldered to a small electronic connector) was inserted through a hole in dura mater into the right lateral ventricle.

As shown in FIG. 2A, bromophenol blue dye was stereotaxically delivered into both hemispheres of the rat brain at designated coordinates 120 and 122. By using the left hemisphere as a diffusion control, this experimental setup allowed pairwise comparisons within the same animal, thereby ruling out any other effects that might effect a directed migration of the dye in the brain.

Control circuitry was activated to apply a constant-polarity (DC) current to only the right hemisphere, between first and second electrodes 130 and 132, configuring first electrode 130 as a cathode and second electrode 132 as an anode, because bromophenol blue dye comprises effectively anionic (negatively-charged) molecules. The current was applied by repeatedly alternating between two modes: (a) a first mode, in which the current was applied continuously for 5 minutes at a magnitude of 1-2 mA, and (b) a second mode, in which the current was applied in 10-ms-duration pulses, one pulse per second (i.e., a pulse frequency of 1 Hz), at a magnitude of 1-2 mA.

FIG. 2B shows the displacement of the bromophenol blue dye after application of the current to the right hemisphere. As can be seen, the bromophenol blue dye in the left hemisphere experienced minimal dispersion and no directed displacement. In contrast, in the right hemisphere, the applied current moved the bromophenol blue dye toward the lateral ventricle. The dye moved with the average velocity of 0.28+/−0.006 mm/min, which was more than 14 times greater than the observed diffusion rate in the left hemisphere. In the right hemisphere, the linear displacement of the dye profile center was about 1.9±0.08 mm, while the front of the dye profile reached a maximum distance of about 2.81±0.07 mm from the center of the injection point.

The results of this experiment demonstrated that molecules of dye can be moved within brain tissue by applying a DC current using two electrodes implanted in the brain, and that in such a setup, a natural migration path is toward the ventricles. The inventors believe that application of the current between the electrodes may have moved the dye electrophoretically. The inventors also believe that implantation of the first electrode directly in brain parenchyma, rather than in the superior sagittal sinus, may provide even better current-driven movement of molecules, because the resistance of the parenchyma-sinus interface was calculated as more than two-fold higher than the resistance measured within the parenchyma, based on data collected during the experiment.

Amyloid Beta Mobility and Directionality Assessment

Figure 3:
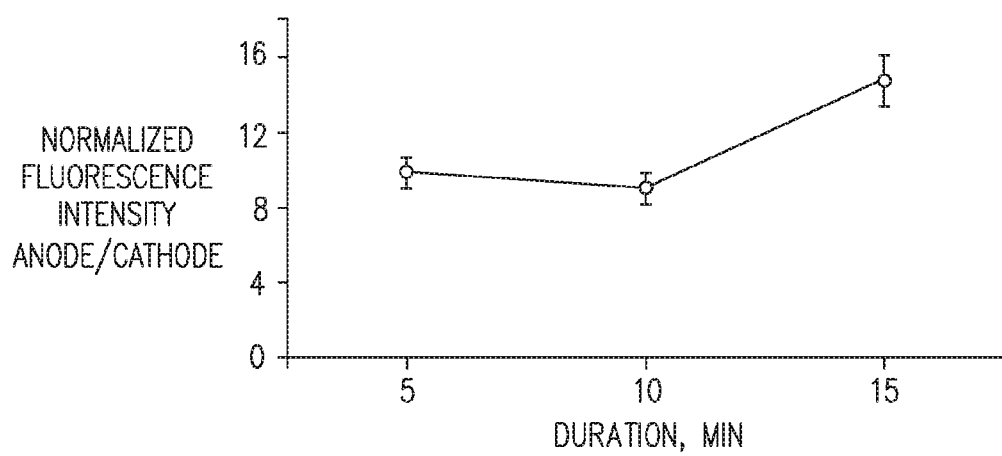
FIG. 3 is a graph showing results of an in vitro experiment performed in accordance with an application of the present invention.

Reference is now made to FIG. 3, which is a graph showing results of an in vitro experiment performed in accordance with an application of the present invention. The experiment assessed the extent to which application of direct current (DC) eliminated amyloid beta peptides from an artificial cerebrospinal fluid (aCSF) solution (comprising phosphate buffered saline (PBS) solution). Pt—Ir electrodes were inserted into a compartment filled with the aCSF solution. Fluorophore-tagged amyloid beta peptides were dissolved to three different dilution levels (2:500, 5:500, and 10:500). Constant DC currents of three different durations (5, 10, and 15 minutes) were applied from a 1.5 V alkaline battery to the aCSF solution containing the fluorophore-tagged amyloid beta peptides. The directionality and overall capability of amyloid beta to undergo electrophoretic movement was assessed by densitometric analysis of fluorescence on each electrode.

The fluorescence intensity was measured at both electrodes, and the fluorescence intensity was normalized at the positively-charged electrode (anode) with respect to the negatively-charged electrode (cathode) by taking the ratio of fluorescence. Data was averaged from all the measurements and is presented as mean and standard error of mean in FIG. 3.

As can be seen in FIG. 3, current-duration-dependent enhancement of fluorescence was observed near the positively-charged electrode (anode) (for the 2:500 dilution level). The difference in fluorescence between the anodes and the cathodes was statistically significant (one tailed t-test: $p<10^{-15}$; $t=12.17$) for the current-duration-dependent analysis. The current-duration-dependent trend of fluorescence enhancement on the positively-charged electrode was also statistically significant for 15-minute current application vs. 5- and 10-minute current application (one-way ANOVA: $p<0.001$, $F=8.92$; Holm-Sidak post-hoc analysis: $p<0.01$, $t=3.37$ for 15 minutes vs. 5 minutes and $t=3.889$ for 15 minutes vs. 10 minutes due to nonspecific binding). At all concentrations there was significant attraction of the amyloid beta to the anode vs. the cathode.

These experimental results demonstrate that soluble monomeric amyloid beta in its native conformation is negatively charged in aCSF and is capable of moving in the electrical field without the need to add any amphiphilic detergents to provide the negative charge to the amyloid beta.

Amyloid Beta Electrophoretic Mobility Assessment in Wild Type Mouse Brain Parenchyma An animal experiment was performed in accordance with an application of the present invention. 20 three-month wild-type mice were anesthetized, and soluble fluorophore-tagged amyloid beta (1-42), HiLyte™ Fluor 488-labeled, Human (AnaSpec, USA) was injected into the brain parenchyma (AP=−2, ML=0.84, DV=1.2). A first Pt—Ir electrode was implanted in brain parenchyma (AP=−2.8, ML=0.84, DV=1.5), and a second Pt—Ir electrode was implanted in the lateral ventricle (AP=−0.5, ML=0.84, DV=1.6). An electrical field generated by the current between the electrodes covered the amyloid beta injection focus. The current application was applied by the repetition of single pulses. The following parameters were used: voltage: 70 V; and frequency: 1 Hz. The current application protocol was as follows: (a) 15 minutes with a pulse duration of 1 ms; (b) 15 minutes with a pulse duration of 10 ms; and (c) 15 minutes with a pulse duration of 100 ms. The frequency was kept constant but the duty cycle was increased.

Assessment of amyloid beta movement directionality in the electrical field was conducted by using antibodies directed against 1-16 amino acid strip of 6E10 (Catalog no. SIG-39320) to visualize the traces of amyloid beta peptide movement in the electrical field. Tissue structure and cell nuclei were visualized by DAPI staining. Amyloid beta movement trajectory was evaluated at different magnifications (4× and 10×). Sagittal slices were stained with anti- bodies against cell nuclei (blue) and amyloid beta (6E10, green), and imaged by fluorescence microscopy.

Amyloid beta movement was visualized in mouse brains to which the electrical current was applied. The electrode inserted into the lateral ventricle was positively charged, and, similarly to the in vitro experiment described hereinabove with reference to FIG. 3, the applied current was capable of inducing amyloid beta movement.

These experimental results demonstrate that electrophoretic movement of amyloid beta peptides is possible in the brain parenchyma with the electrical current-application protocol used in the experiment. The directionality of amyloid beta peptide movement was similar to that observed the in vitro experiment described hereinabove with reference to FIG. 3.

Reference is made to FIGS. 4A-G, which are schematic illustrations of alternative configurations of system 20, in accordance with respective applications of the present invention. These figures show an anterior view of brain 52. In these applications, system 20 is configured to, in addition to clearing the substance (e.g., the amyloid beta, the metal ions, the tau protein, and/or the waste substance) from brain parenchyma 50 into the CSF-filled space, to clear the substance from the CSF-filled space (e.g., subarachnoid space 144) to superior sagittal sinus 142. These techniques may be used in combination with any of the techniques described hereinabove. For some of these techniques, control circuitry 34 is configured to apply the treatment current as direct current.

For some applications described with reference to FIGS. 4A-G, control circuitry 34 is configured to simultaneously drive electrodes to both (a) clear the substance from brain parenchyma 50 into the CSF-filled space, and (b) clear the substance from the CSF-filled space to superior sagittal sinus 142. For example, control circuitry 34 may be configured to apply different respective voltages to parenchymal electrode 30, CSF electrode 32, and a midplane treatment electrode 150, described below. For example, control circuitry 34 may be configured to apply first, second, and third voltages to parenchymal electrode 30, CSF electrode 32, and midplane treatment electrode 150, respectively, the third voltage more positive than the second voltage, which is in turn more positive than first voltage. The total potential difference between the first and the third voltages is typically no greater than 1.2 V volt to avoid electrolysis in the vicinity of one or both of the electrodes.

For other applications described with reference to FIGS. 4A-G, control circuitry 34 is configured to alternatingly drive sets of the electrodes, such as (a) during a plurality of first time periods, driving parenchymal electrode 30 and CSF electrode 32, in order to clear the substance from brain parenchyma 50 into the CSF-filled space, and (b) during a plurality of second time periods, typically not overlapping with the first time periods, driving midplane treatment electrode 150 and either CSF electrode 32 or another electrode (described below), in order to clear the substance from the CSF-filled space to superior sagittal sinus 142.

For some applications described with reference to FIGS. 4A-G, control circuitry 34 is configured to clear the substance to superior sagittal sinus 142 by electroosmotically driving fluid from the CSF-filled space (e.g., subarachnoid space 144) to superior sagittal sinus 142. For some applications, control circuitry 34 is configured to drive the fluid from the CSF-filled space of the brain to superior sagittal sinus 142 by configuring midplane treatment electrode 150 as a cathode, and CSF electrode 32 as an anode.

For some applications described with reference to FIGS. 4A-G, control circuitry 34 is configured to clear the substance by electrophoretically driving the substance from the CSF-filled space (e.g., subarachnoid space 144) to superior sagittal sinus 142. For some applications, application of the treatment current causes a potential difference between the CSF-filled space and superior sagittal sinus 142, which causes movement of the substance from the CSF-filled space to superior sagittal sinus 142.

Figure 4A:
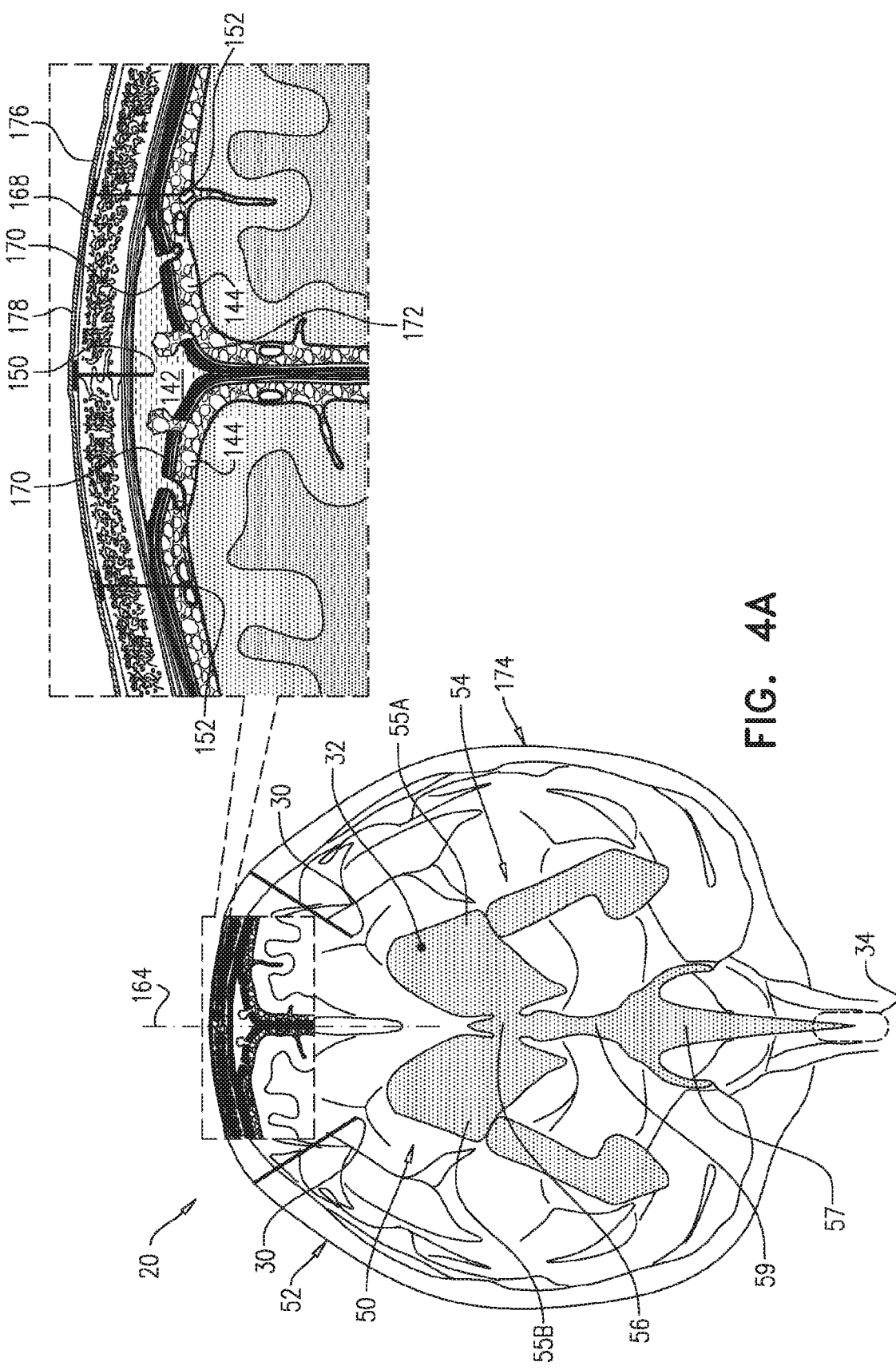
FIGS. 4A-G are schematic illustrations of alternative configurations of the system of FIGS. 1A-C, in accordance with respective applications of the present invention.

For some applications, such as shown in FIG. 4A, parenchymal electrode 30 is implanted in brain parenchyma 50, and CSF electrode 32 is implanted in the CSF-filled space, such as ventricular system 54 or subarachnoid space 144. A midplane treatment electrode 150 is disposed either (a) in superior sagittal sinus 142 (as shown in FIG. 4A), or (b) over superior sagittal sinus 142 (configuration not shown in FIG. 4A, but shown in FIGS. 4B-G). A second CSF electrode 152 is implanted the CSF-filled space, such as ventricular system 54 (configuration not shown in FIG. 4A) or subarachnoid space 144 (as shown in FIG. 4A). Control circuitry 34 is activated to apply (a) a first voltage between parenchymal electrode 30 and CSF electrode 32, to clear the substance from brain parenchyma 50 into the CSF-filled space, and (b) a second voltage between midplane treatment electrode 150 and second CSF electrode 152, to clear the substance from the CSF-filled space to superior sagittal sinus 142. This technique may be used in combination with the techniques described hereinbelow with reference to FIGS. 4B-G, mutatis mutandis.

Figure 4B:
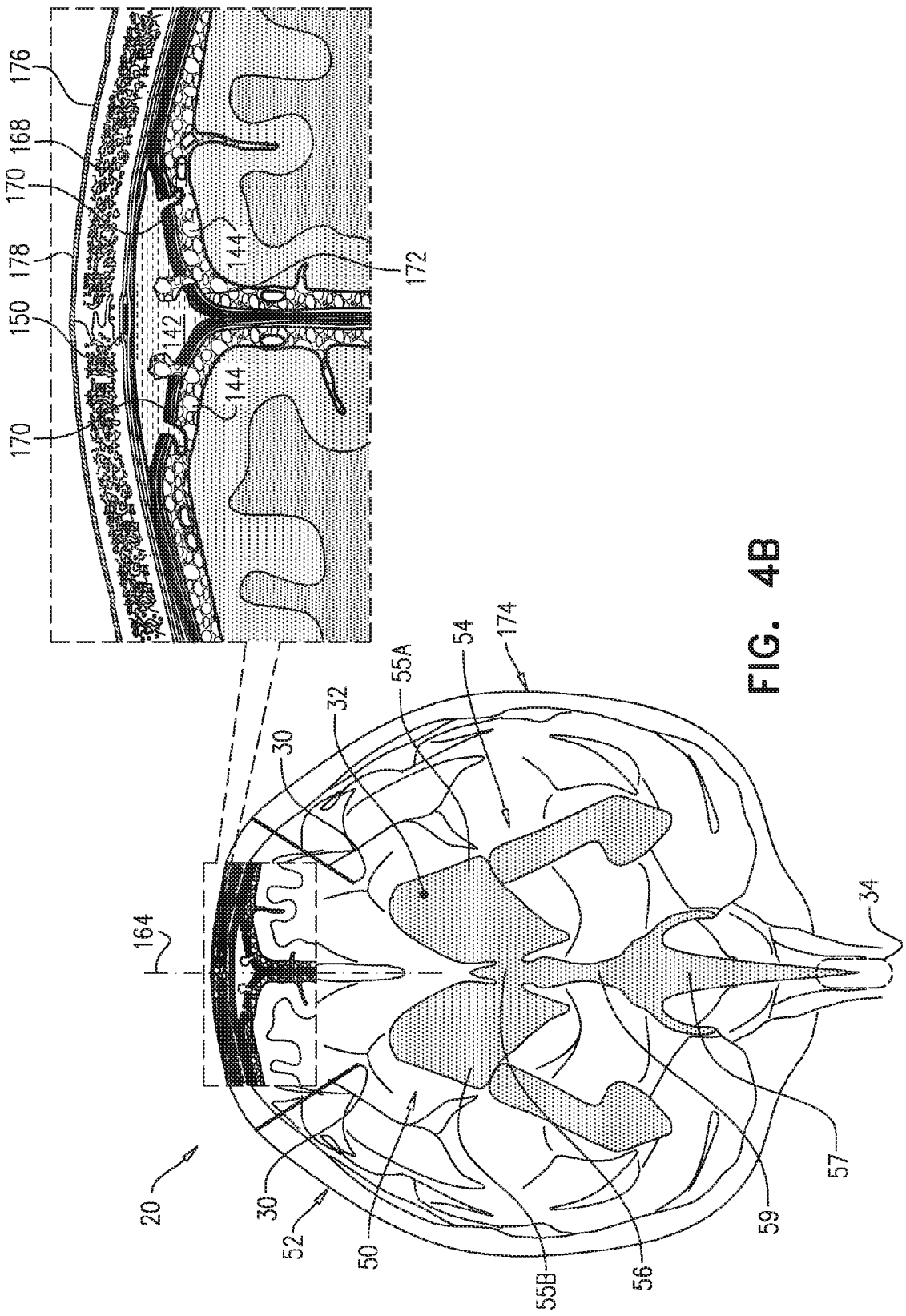

Alternatively, for some applications, such as shown in FIG. 4B, parenchymal electrode 30 is implanted in brain parenchyma 50, and CSF electrode 32 is implanted in the CSF-filled space, such as ventricular system 54 or subarachnoid space 144. Midplane treatment electrode 150 is disposed either (a) in superior sagittal sinus 142 (as shown in FIG. 4A), or (b) over superior sagittal sinus 142 (as shown in FIGS. 4B-G). Control circuitry 34 is activated to apply (a) a first voltage between parenchymal electrode 30 and CSF electrode 32, to clear the substance from brain parenchyma 50 into the CSF-filled space, and (b) a second voltage between CSF electrode 32 and midplane treatment electrode 150, to clear the substance from the CSF-filled space to superior sagittal sinus 142.

Figure 4C:
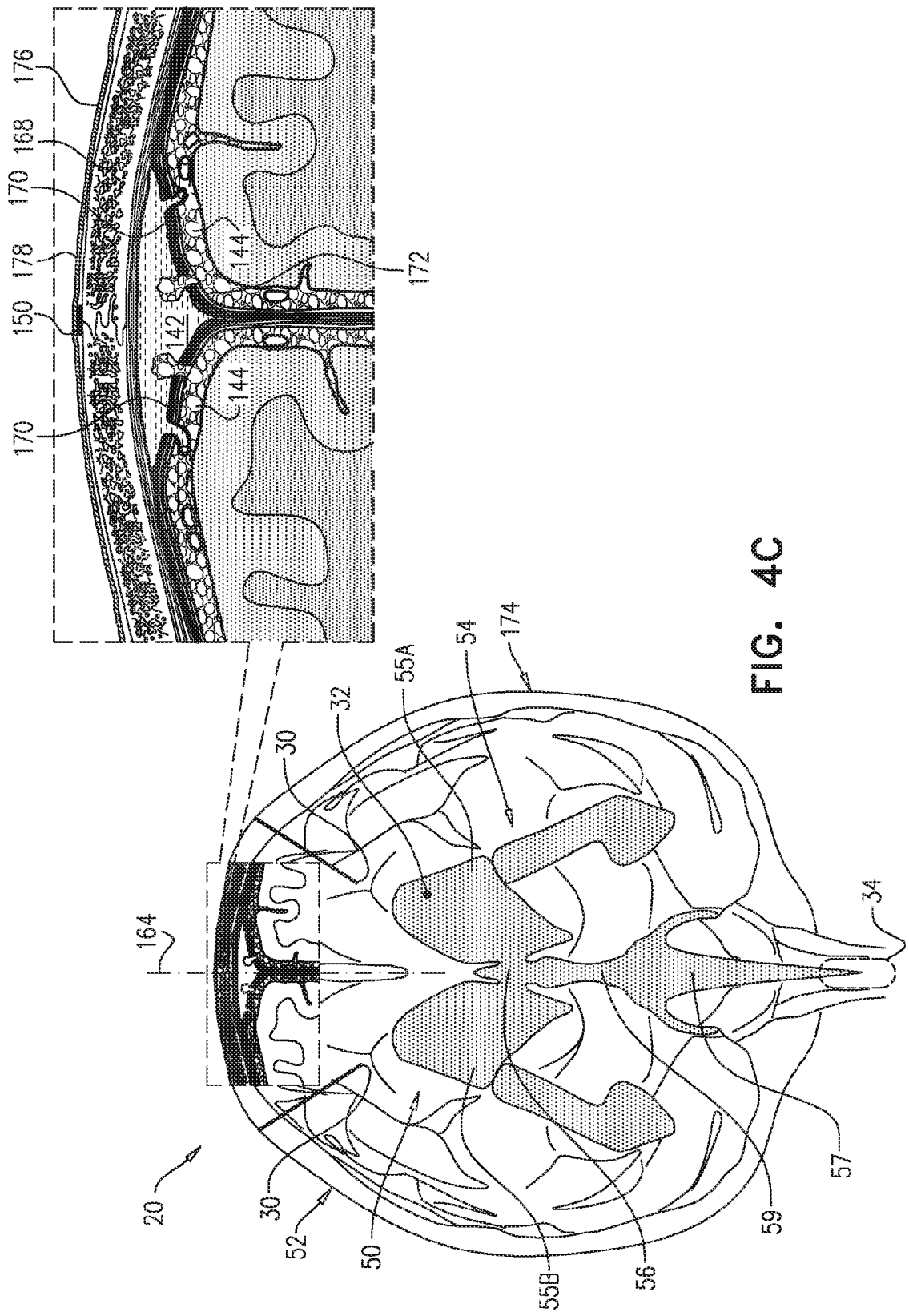

For some applications, such as shown in FIGS. 4B-C, midplane treatment electrode 150 is adapted to be disposed over superior sagittal sinus 142. For some of these applications, midplane treatment electrode 150 is adapted to be disposed under a skull 168 of a head 174 of the subject, such as in contact with an outer surface of superior sagittal sinus 142 (either under the dura mater or in contact with an outer surface of the dura mater). For others of these applications, midplane treatment electrode 150 is adapted to be disposed outside and in electrical contact with skull 168. As used in the present application, including in the claims, "over the superior sagittal sinus" means aligned with the superior sagittal sinus at a location more superficial than the superior sagittal sinus, i.e., at a greater distance from a center of the head. In the configurations shown in FIGS. 4B and 4C, control circuitry 34 is configured to clear the substance from the CSF-filled space to superior sagittal sinus 142, by applying a treatment current between midplane treatment electrode 150 and CSF electrode 32. Alternatively, the placements of midplane treatment electrode 150 shown in FIGS. 4B and 4C are used in combination with the configuration described hereinabove with reference to FIG. 4A.

Figure 4D:
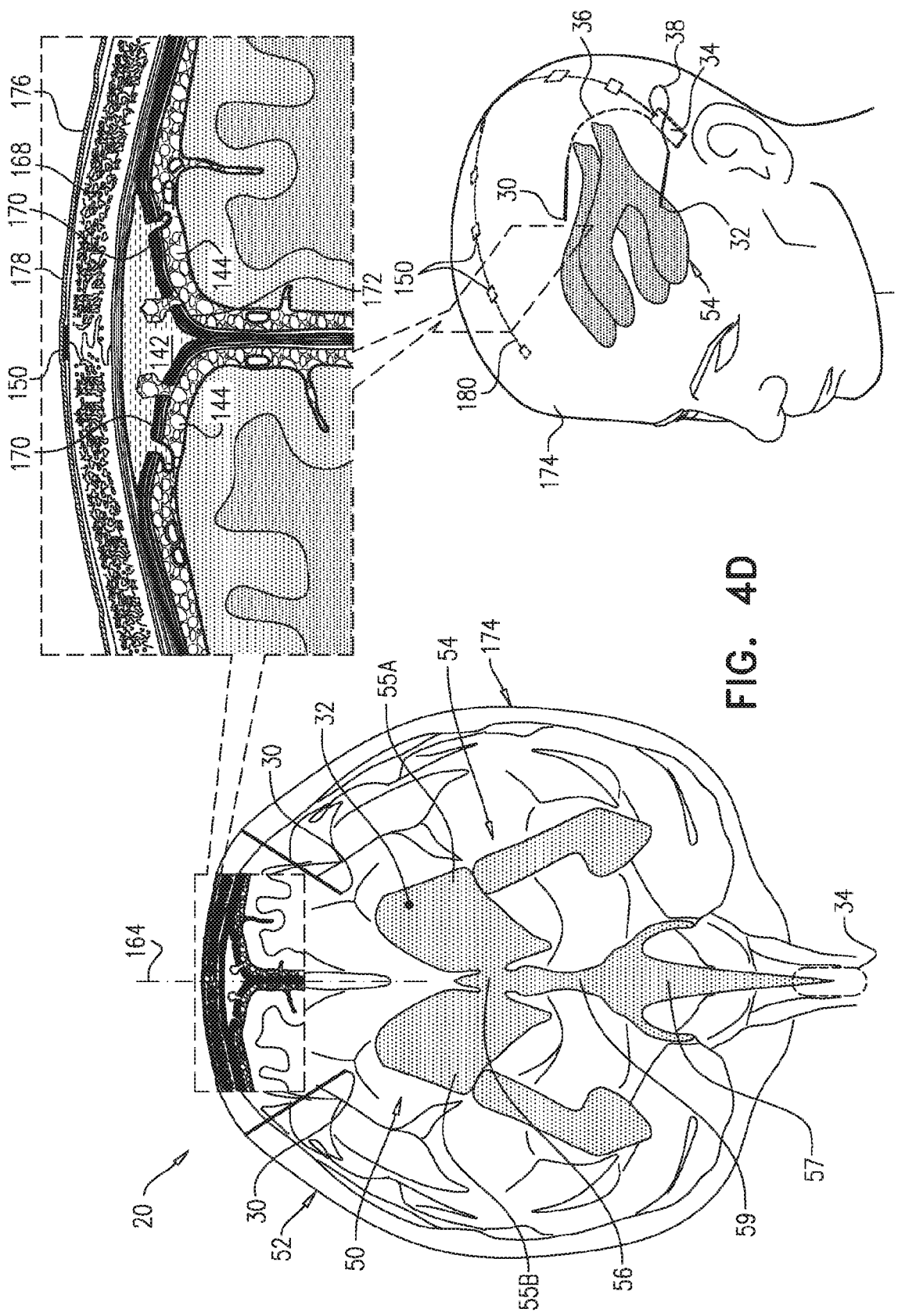

For some applications, such as shown in FIG. 4D, system 20 comprises a plurality of midplane treatment electrodes 150, such as at least 5, no more than 20, and/or between 5 and 20 midplane treatment electrodes 150. Midplane treatment electrodes 150 are disposed either (a) in superior sagittal sinus 142 (configuration not shown in FIG. 4D, but shown in FIG. 4A), or (b) over superior sagittal sinus 142 (as shown in FIG. 4D, or in FIG. 4B).

For any of the applications described herein, including, but not limited to those described with reference to FIGS. 4A-G, CSF electrode 32 may be adapted to be disposed between 1 and 12 cm of a sagittal midplane 164 of skull 168. For some applications, the method may comprise implanting CSF electrode 32 between 1 and 12 cm of sagittal midplane 164 of skull 168.

For any of the applications described herein, including, but not limited to those described with reference to FIGS. 4A-G, the CSF-filled space may be subarachnoid space 144, CSF electrode 32 may be a subarachnoid electrode, configured to be implanted in subarachnoid space 144, and control circuitry 34 may be configured to clear the substance from subarachnoid space 144 to superior sagittal sinus 142.

Figure 4E:
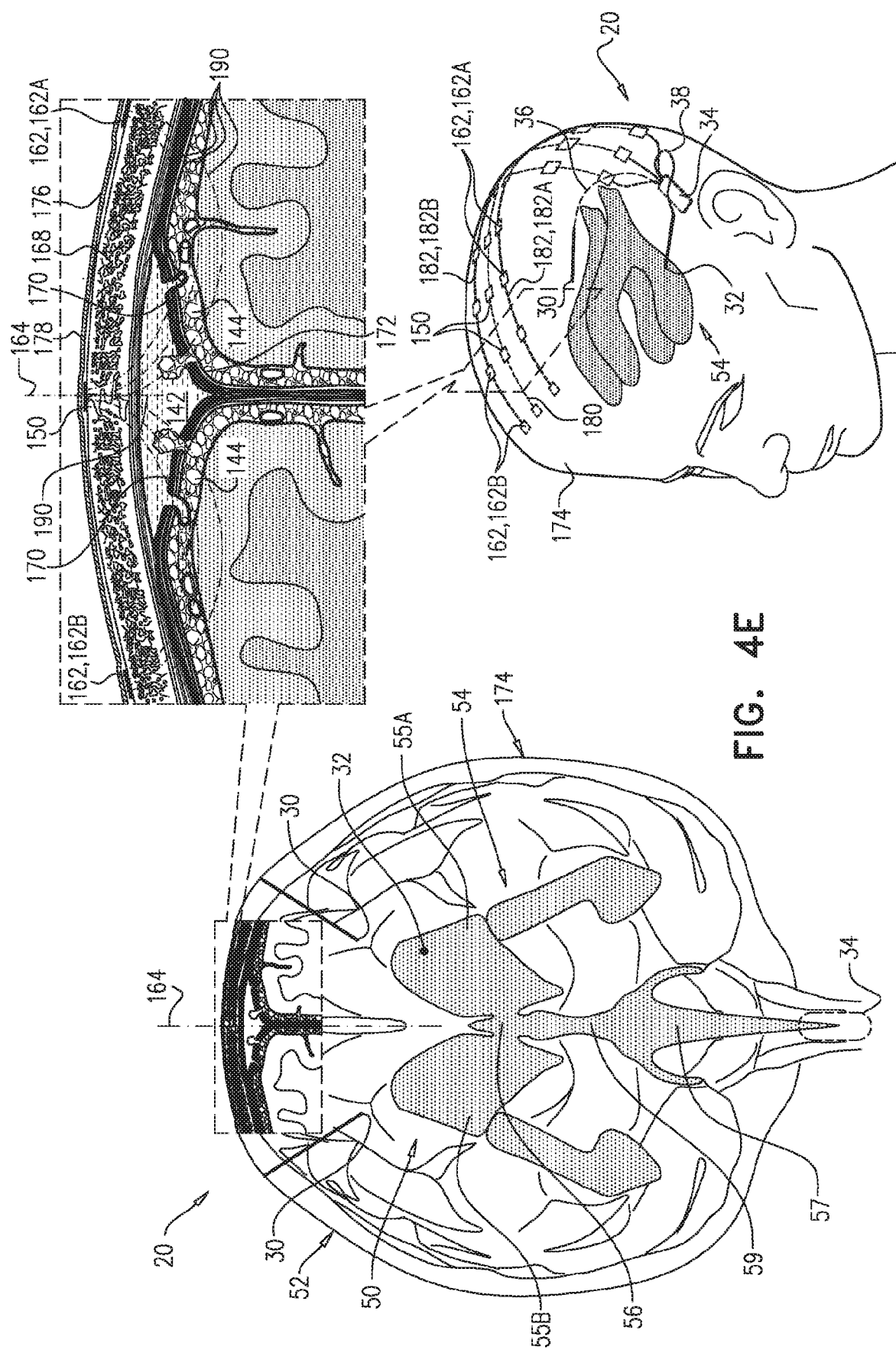
Figure 4F:
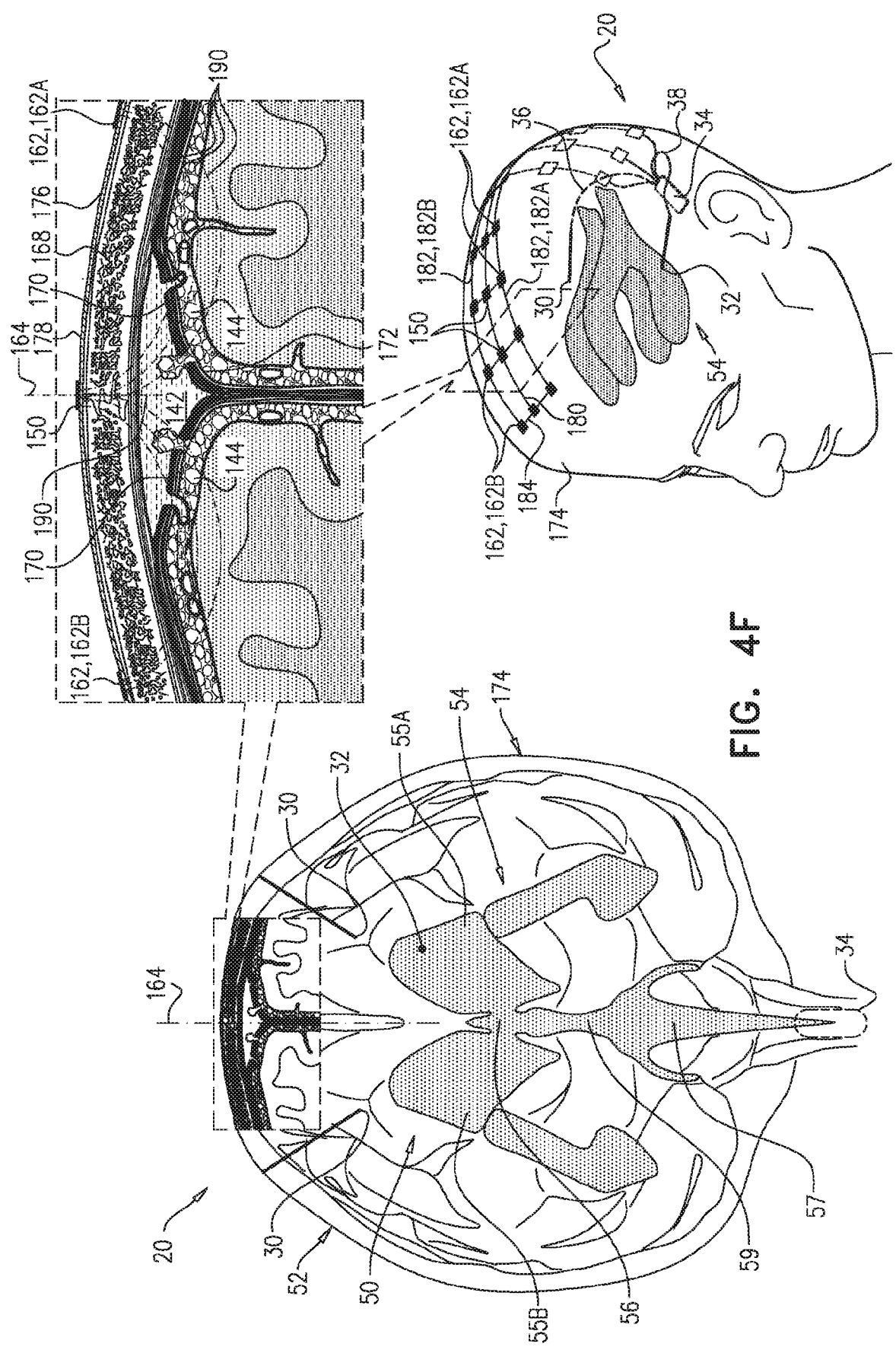
Figure 4G:
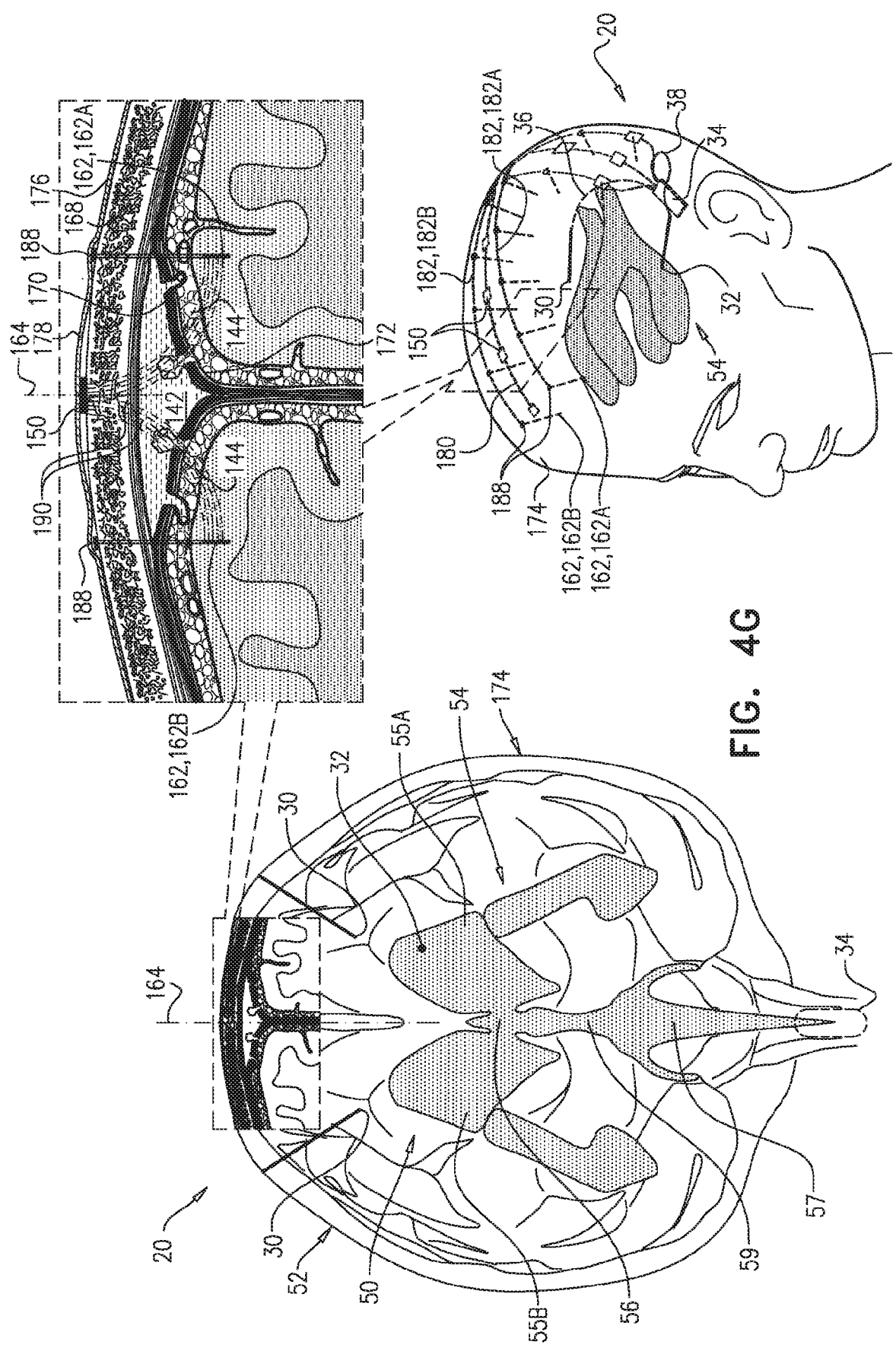

For some applications, such as shown in FIG. 4E-G, system 20 comprises (a) midplane treatment electrodes 150, adapted to be disposed over superior sagittal sinus 142, outside and in electrical contact with skull 168, and (b) lateral treatment electrodes 162, adapted to be disposed at a distance of between 1 and 12 cm of sagittal midplane 164 of skull 168 (the distance is measured in a straight line from a closest portion of each treatment electrode to sagittal midplane 164, rather than along the curvature of skull 168). Control circuitry 34 is configured to clear the substance from subarachnoid space 144 to superior sagittal sinus 142, by applying one or more treatment currents between (a) one or more of midplane treatment electrodes 150 and (b) one or more of lateral treatment electrodes 162 (each of the treatment currents is schematically illustrated in the figures by a plurality of current lines 190).

For some applications, system 20 comprises as at least 5, no more than 40, and/or between 5 and 40 lateral treatment electrodes 162, such as between 5 and 20 lateral treatment electrodes 162, or between 10 and 40 lateral treatment electrodes. For some applications, the number of each type of treatment electrode is determined based on the size of head 174 of the subject. For some applications, system 20 comprises twice as many lateral treatment electrodes 162 as midplane treatment electrodes 150.

For some applications, the one or more treatment currents applied using midplane treatment electrodes 150 and lateral treatment electrodes 162 pass between subarachnoid space 144 and superior sagittal sinus 142, via inferolateral surfaces 170 of superior sagittal sinus 142. For some of these applications, at least 40%, e.g., at least 75% or at least 90%, of the treatment currents pass between subarachnoid space 144 and superior sagittal sinus 142, via inferolateral surfaces 170 of superior sagittal sinus 142. For the applications described immediately above, the locations of midplane treatment electrodes 150 and/or lateral treatment electrodes 162 are typically selected such that the one or more treatment currents pass through inferolateral surfaces 170. For example, for configurations in which lateral treatment electrodes 162 are disposed outside and in electrical contact with skull 168, such as described with reference to FIGS. 4C-G, lateral treatment electrodes 162 may be disposed at a distance of at least 4 cm, no more than 12 cm, and/or between 4 and 12 cm of sagittal midplane 164 of skull 168; for configurations in which lateral treatment electrodes 162 are implanted under an arachnoid mater 172 of the subject, such as described with reference to FIGS. 4C-G, lateral treatment electrodes 162 may be disposed at least 1 cm, no more than 3 cm, and/or between 1 and 3 cm of sagittal midplane 164 of skull 168.

For some applications, at least five midplane treatment electrodes 150 are disposed over superior sagittal sinus 142. Alternatively or additionally, for some applications, at least five lateral treatment electrodes 162 between 1 and 12 cm of sagittal midplane 164 of skull 168. For some applications, each of lateral treatment electrodes 162 is disposed between 1 and 12 cm of at least one of midplane treatment electrodes 150.

For some applications, midplane treatment electrodes 150 are disposed within 10 mm of sagittal midplane 164 of skull 168. Alternatively or additionally, for some applications, midplane treatment electrodes 150 are disposed such that at least one of midplane treatment electrodes 150 is at least 5 mm from another one of midplane treatment electrodes 150, no more than 20 mm from another one of midplane treatment electrodes 150, and/or between 5 and 150 mm from another one of midplane treatment electrodes 150. For some applications, at least one of lateral treatment electrodes 162 is disposed is at least 5 mm from another one of lateral treatment electrodes 162.

For some applications, such as shown in FIG. 4E, midplane treatment electrodes 150 are implanted under skin 176 of head 174. For other applications, such as shown in FIG. 4F, midplane treatment electrodes 150 are disposed outside head 174, such as on an external surface 178 of head 174.

For some applications, system 20 further comprises a midplane lead 180, along which midplane treatment electrodes 150 are disposed (e.g., fixed). Midplane lead 180 is disposed outside skull 168 in order to dispose midplane treatment electrodes 150 over superior sagittal sinus 142. For some applications in which midplane treatment electrodes 150 are implanted under skin 176, the implantation is performed by introducing midplane lead 180 through an incision in skin 176, typically at a posterior site of the head, and tunneling the midplane lead toward an anterior site of the head, such as near the forehead. Optionally, each of midplane treatment electrodes 150 is inserted through a respective incision in skin 176, and connected to midplane lead 180.

For some applications, such as shown in FIGS. 4E-F, lateral treatment electrodes 162 are disposed outside and in electrical contact with skull 168. For some of these applications, lateral treatment electrodes 162 are implanted under skin 176 of head 174, such as shown in FIG. 4E. Alternatively, lateral treatment electrodes 162 are disposed outside head 174, such as on external surface 178 of head 174, such as shown in FIG. 4F. For some of these applications, lateral treatment electrodes 162 may be disposed at least 4 cm, no more than 12 cm, and/or between 4 and 12 cm of sagittal midplane 164 of skull 168. (As used in the present application, including in the claims, all specified ranges include their endpoints.) Such positioning may generate one or more treatment currents that pass between subarachnoid space 144 and superior sagittal sinus 142, via inferolateral surfaces 170 of superior sagittal sinus 142, as described above.

For some applications, system 20 further comprises a lateral lead 182, along which lateral treatment electrodes 162 are disposed (e.g., fixed). Lateral lead 182 is disposed outside skull 168, typically within 1 and 12 cm of sagittal midplane 164 of skull 168, in order to dispose lateral treatment electrodes 162. For some applications in which lateral treatment electrodes 162 are implanted under skin 176, the implantation is performed by introducing lateral lead 182 through an incision in skin 176, typically at a posterior site of the head, and tunneling the lateral lead toward an anterior site of the head, such as near the forehead. Optionally, each of lateral treatment electrodes 162 is inserted through a respective incision in skin 176, and connected to lateral lead 182. For some applications, instead of providing lateral lead 182, lateral treatment electrodes 162 are instead coupled to midplane lead 180. Midplane lead 180 is introduced with the lateral electrodes constrained, and, the lateral electrodes are configured upon release to extend laterally, typically automatically. This configuration may also be used for applications in which both left and right lateral electrodes are provided, as described hereinbelow.

For some applications, control circuitry 34 is activated to independently apply the treatment currents between respective pairs of midplane treatment electrodes 150 and lateral treatment electrodes 162. Such independent application of the currents allows continued effective operation of system 20 even if a low resistance should develop between the electrodes of one of the pairs (e.g., because of anatomical variations). For some of these applications, in order to enable such independent application of the currents, midplane lead 180 comprises a plurality of conductive wires corresponding to a number of midplane treatment electrodes 150, and lateral lead 182 comprises a plurality of conductive wires corresponding to a number of lateral treatment electrodes 162. Alternatively, control circuitry 34 and the electrodes implement electrical multiplexing, as is known in the art, in which case each of the leads need only comprise a single conductive wire. Alternatively, for some applications, all of midplane treatment electrodes 150 are electrically coupled to one another (such as by a single conductive wire in the midplane lead), and all of lateral treatment electrodes 162 are electrically coupled to one other (such as by a single conductive wire in the lateral lead).

For some applications of the configuration shown in FIG. 4F, system 20 further comprises one or more thin elongate support elements 184, which couple lateral leads 182 to midplane lead 180, in order to provide proper spacing and alignment between the midplane electrodes and the lateral electrodes. Support elements 184 are typically non-conductive.

For some applications described with reference to FIGS. 4A-G, control circuitry 34 is configured to apply the one or more treatment currents with an average amplitude of between 1 and 3 milliamps. (The resulting voltage is typically greater in the configuration shown in FIGS. 4E-F than in the configuration shown in FIG. 4G, because the one or more treatment currents pass through skull 168 twice.)

For some applications described with reference to FIGS. 4A-G, control circuitry 34 is activated to apply the one or more treatment currents as direct current, typically as a plurality of pulses, for example at greater than 500 Hz and/or less than 2 kHz, e.g., at 1 kHz. For some applications, a duty cycle of the pulses is above 90%, and for some applications pulses are not used but instead an effective duty cycle of 100% is utilized. Typically, but not necessarily, the duty cycle is 90% or lower, because a given level of applied voltage produces higher current in the tissue if the capacitance in the tissue is allowed to discharge between pulses. For other applications, control circuitry 34 is activated to apply the one or more treatment currents as alternating current with a direct current offset and a constant polarity. For example, the frequency may be at least 1 Hz, no more than 100 Hz (e.g., no more than 10 Hz), and/or between 1 Hz and 100 Hz (e.g., between 1 Hz and 10 Hz).

As mentioned above, for some applications, control circuitry 34 is configured to clear the substance by electroosmotically driving fluid from subarachnoid space 144 to superior sagittal sinus 142. For some applications, control circuitry 34 is configured to configure midplane treatment electrodes 150 as cathodes, and lateral treatment electrodes 162 as anodes. Alternatively or additionally, increased flow of cerebrospinal fluid (CSF) out of the brain's ventricular system via subarachnoid space 144, as a result of the applied voltage, may itself treat Alzheimer's disease and/or CAA, independent of any direct clearance of beta amyloid in the CSF flow.

For some applications, lateral treatment electrodes 162 comprise (a) left lateral treatment electrodes 162A, which are adapted to be disposed left of sagittal midplane 164 of skull 168, and (b) right lateral treatment electrodes 162B, which are adapted to be disposed right of sagittal midplane 164 of skull 168. For some applications, control circuitry 34 is configured to configure midplane treatment electrodes 150 as cathodes, and left and right lateral treatment electrodes 162A and 162B as left and right anodes, respectively.

As mentioned above, for some applications, control circuitry 34 is configured to clear the substance by electrophoretically driving the substance from subarachnoid space 144 to superior sagittal sinus 142. For some applications, lateral treatment electrodes 162 comprise (a) left lateral treatment electrodes 162A, which are adapted to be disposed left of sagittal midplane 164 of skull 168, and (b) right lateral treatment electrodes 162B, which are adapted to be disposed right of sagittal midplane 164 of skull 168. For some of these applications, control circuitry 34 is configured to configure the midplane treatment electrodes 150 as anodes, and left and right lateral treatment electrodes 162A and 162B as left and right cathodes, respectively. In experiments conducted on behalf of the inventor, amyloid beta was found to be attracted to the positive electrode (anode).

For some applications, lateral treatment electrodes 162 are adapted to be implanted under an arachnoid mater 172 of the subject, such as in brain parenchyma 50 (gray or white matter), as shown in FIG. 4G, or in subarachnoid space 144, such as shown in FIG. 4A. For some applications, the same electrodes serve as both parenchymal electrode 30 and lateral treatment electrodes 162, and are driven by control circuitry 34 either at the same time or at different times. For example, lateral treatment electrodes 162 may comprise needle electrodes, as is known in the art; optionally, lateral treatment electrodes 162 comprise respective proximal anchors 188. This configuration may implement any of the techniques described hereinabove with reference to FIGS. 4A-F, mutatis mutandis.

For some of these applications, lateral treatment electrodes 162 are disposed at least 1 cm, no more than 3 cm, and/or between 1 and 3 cm of sagittal midplane 164 of skull 168. Such positioning may generate the treatment currents that pass between subarachnoid space 144 and superior sagittal sinus 142, via inferolateral surfaces 170 of superior sagittal sinus 142, as described above. For some applications, each of lateral treatment electrodes 162 is disposed between 1 and 3 cm of at least one of midplane treatment electrodes 150. For some applications, each of lateral treatment electrodes 162 is disposed between 1 and 3 cm of one of midplane treatment electrodes 150 that is closest to the lateral treatment electrode.

As mentioned above, for some applications, system 20 further comprises midplane lead 180, along which midplane treatment electrodes 150 are disposed (e.g., fixed). Midplane lead 180 is disposed outside skull 168 in order to dispose midplane treatment electrodes 150. For some of these applications, system 20 further comprises (a) a left lateral lead 182A, along which left lateral treatment electrodes 162A are disposed (e.g., fixed), and (b) a right lateral lead 182B, along which right lateral treatment electrodes 162B are disposed (e.g., fixed). Left lateral lead 186A is disposed outside skull 168, typically within 1 and 12 cm of sagittal midplane 164 of skull 168, in order to dispose left lateral treatment electrodes 162A. Right lateral lead 186B is disposed outside skull 168, typically within 1 and 12 cm of sagittal midplane 164 of skull 168, in order to dispose right lateral treatment electrodes 162B.

Reference is again made to 4A-G. For some applications, control circuitry 34 is configured to detect a voltage difference between subarachnoid space 144 and superior sagittal sinus 142, and set a level of the one or more treatment currents responsively to the detected voltage difference.

Although some of the techniques described hereinabove have been described as treating the subject by electroosmotically driving fluid from subarachnoid space 144 to superior sagittal sinus 142, the techniques may alternatively or additionally be used without electroosmosis.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. application Ser. No. 13/872,794, filed Apr. 20, 2013, which published as US Patent Application Publication 2014/0324128;

U.S. application Ser. No. 14/794,739, filed Jul. 8, 2015, which issued as U.S. Pat. No. 9,616,221;

International Application PCT/IL2016/050728, filed Jul. 7, 2016, which published as PCT Publication WO 2017/006327; and U.S. application Ser. No. 14/926,705, filed Oct. 29, 2015, which issued as U.S. Pat. No. 9,724,515.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:

implanting a parenchymal electrode in or in contact with an outer surface of brain parenchyma of a subject identified as at risk of or suffering from a disease;

implanting a cerebrospinal fluid (CSF) electrode in a CSF-filled space of a brain of the subject, the CSF-filled space selected from the group consisting of: a ventricular system and a subarachnoid space;

disposing a midplane treatment electrode in or over a superior sagittal sinus; and activating control circuitry to:

drive the parenchymal electrode and the CSF electrode to drive a substance from the brain parenchyma into the CSF-filled space of the brain by applying direct current between the parenchymal electrode and the CSF electrode with an average amplitude of between 1 and 5 mA, the substance comprising one or more substances selected from the group of substances consisting of: amyloid beta, tau protein, and metal ions, and apply treatment direct current, with an average amplitude of between 1 and 3 mA, between the CSF electrode and the midplane treatment electrode to drive the substance from the CSF-filled space of the brain to the superior sagittal sinus.

2. The method according to claim 1, wherein the disease is Alzheimer's disease, and wherein implanting parenchymal electrode comprises implanting the parenchymal electrode in the subject identified as at risk of or suffering from Alzheimer's disease.

3. The method according to claim 1, wherein the disease is cerebral amyloid angiopathy (CAA), and wherein implanting parenchymal electrode comprises implanting the parenchymal electrode in the subject identified as at risk of or suffering from CAA.

4. The method according to claim 1, wherein the CSF-filled space of the brain is the ventricular system, wherein the CSF electrode is a ventricular electrode, and wherein activating the control circuitry comprises activating the control circuitry to drive the parenchymal electrode and the ventricular electrode to drive the substance from the brain parenchyma into the ventricular system.

5. The method according to claim 1, wherein the CSF-filled space of the brain is the subarachnoid space, wherein the CSF electrode is a subarachnoid electrode, and wherein activating the control circuitry comprises activating the control circuitry to drive the parenchymal electrode and the subarachnoid electrode to drive the substance from the brain parenchyma into the subarachnoid space.

6. The method according to claim 1, wherein the substance includes amyloid beta, and wherein activating the control circuitry comprises activating the control circuitry to drive the parenchymal electrode and the CSF electrode to drive the amyloid beta from the brain parenchyma into the CSF-filled space of the brain.

7. The method according to claim 1, wherein the substance includes metal ions, and wherein activating the control circuitry comprises activating the control circuitry to drive the parenchymal electrode and the CSF electrode to drive the metal ions from the brain parenchyma into the CSF-filled space of the brain.

8. The method according to claim 1, wherein the substance includes tau protein, and wherein activating the control circuitry comprises activating the control circuitry to drive the parenchymal electrode and the CSF electrode to drive the tau protein from the brain parenchyma into the CSF-filled space of the brain.

9. The method according to claim 1, wherein implanting the parenchymal electrode in or in contact with the outer surface of the brain parenchyma comprises implanting the parenchymal electrode in contact with the outer surface of the brain parenchyma.

10. The method according to claim 1, wherein implanting the parenchymal electrode in or in contact with the outer surface of the brain parenchyma comprises implanting the parenchymal electrode in the brain parenchyma.

11. The method according to claim 10, wherein implanting the parenchymal electrode and the CSF electrode comprises implanting the parenchymal electrode and the CSF electrode such that an area of build-up of the substance is between the parenchymal and the CSF electrodes.

12. The method according to claim 10, wherein implanting the parenchymal electrode comprises implanting the parenchymal electrode such that an area of build-up of the substance is between the parenchymal electrode and an area of the CSF-filled space of the brain nearest the area of build-up.

13. The method according to claim 1, further comprising applying deep brain stimulation using the parenchymal electrode.

14. The method according to claim 1, wherein activating the control circuitry to drive the parenchymal electrode and the CSF electrode comprises activating the control circuitry to drive the parenchymal electrode and the CSF electrode to drive the substance by applying the direct current as non-excitatory current between the parenchymal electrode and the CSF electrode.

15. The method according to claim 1, wherein activating the control circuitry to apply the direct current comprises activating the control circuitry to apply the direct current with an average voltage of less than 1.2 V.

16. The method according to claim 1, wherein activating the control circuitry to apply the direct current comprises activating the control circuitry to apply the direct current as a series of pulses at a frequency of between 1 and 10 Hz.

17. The method according to claim 1, wherein disposing the midplane treatment electrode comprises disposing the midplane treatment electrode over the superior sagittal sinus, outside and in electrical contact with a skull of a head of the subject.

18. The method according to claim 1, wherein disposing the midplane treatment electrode comprises implanting the midplane treatment electrode in the superior sagittal sinus.

19. The method according to claim 1,
wherein the CSF-filled space of the brain is the subarachnoid space,
wherein the CSF electrode is a subarachnoid electrode, and
wherein activating the control circuitry comprises activating the control circuitry to drive the substance from the subarachnoid space to the superior sagittal sinus.

20. The method according to claim 1, wherein activating the control circuitry comprises activating the control circuitry to drive the parenchymal electrode and the CSF electrode to drive the substance from the brain parenchyma into the CSF-filled space of the brain by electrophoretically driving the substance from the brain parenchyma into the CSF-filled space of the brain.

21. The method according to claim 1, wherein activating the control circuitry comprises activating the control circuitry to drive the substance from the CSF-filled space of the brain to the superior sagittal sinus by electrophoretically driving the substance from the CSF-filled space of the brain to the superior sagittal sinus.

22. The method according to claim 1, wherein activating the control circuitry comprises activating the control circuitry to drive the parenchymal electrode and the CSF electrode to drive the substance from the brain parenchyma into the CSF-filled space of the brain by electroosmotically driving fluid from the brain parenchyma into the CSF-filled space of the brain.

23. The method according to claim 1, wherein activating the control circuitry comprises activating the control circuitry to drive the substance from the CSF-filled space of the brain to the superior sagittal sinus by electroosmotically driving fluid from the CSF-filled space of the brain to the superior sagittal sinus.

24. The method according to claim 1, wherein activating the control circuitry comprises activating the control circuitry to simultaneously drive (a) the parenchymal electrode and the CSF electrode to drive the substance from the brain parenchyma into the CSF-filled space of the brain, and (b) apply the treatment direct current between the midplane treatment electrode and the CSF electrode to drive the substance from the CSF-filled space to the superior sagittal sinus.

25. The method according to claim 24, wherein activating the control circuitry comprises activating the control circuitry to apply first, second, and third voltages to the parenchymal electrode, the CSF electrode, and the midplane treatment electrode, respectively, the third voltage more positive than the second voltage, which is in turn more positive than first voltage.

26. The method according to claim 1, wherein activating the control circuitry comprises activating the control circuitry to alternatingly (a) drive the parenchymal electrode and the CSF electrode to drive the substance from the brain parenchyma into the CSF-filled space of the brain, and (b) apply the treatment direct current between the midplane treatment electrode and the CSF electrode to drive the substance from the CSF-filled space to the superior sagittal sinus.

27. A method comprising:
implanting a parenchymal electrode in or in contact with an outer surface of brain parenchyma of a subject identified as at risk of or suffering from a disease;
implanting a first cerebrospinal fluid (CSF) electrode in a CSF-filled space of a brain of the subject, the CSF-filled space selected from the group consisting of: a ventricular system and a subarachnoid space;
implanting a second CSF electrode in a CSF-filled space of a brain of the subject, the CSF-filled space selected from the group consisting of: the ventricular system and the subarachnoid space;
disposing a midplane treatment electrode in or over a superior sagittal sinus; and
activating control circuitry to:
drive the parenchymal electrode and the first CSF electrode to drive a substance from the brain parenchyma into the CSF-filled space of the brain, by applying direct current between the parenchymal electrode and the CSF electrode with an average amplitude of between 1 and 5 mA, the substance comprising one or more substances selected from the group of substances consisting of: amyloid beta, tau protein, and metal ions, and apply treatment direct current, with an average amplitude of between 1 and 3 mA, between the second CSF electrode and the midplane treatment electrode to drive the substance from the CSF-filled space of the brain to the superior sagittal sinus.

28. The method according to claim 27, wherein disposing the midplane treatment electrode comprises disposing the midplane treatment electrode over the superior sagittal sinus, outside and in electrical contact with a skull of a head of the subject.

29. The method according to claim 27, wherein disposing the midplane treatment electrode comprises implanting the midplane treatment electrode in the superior sagittal sinus.

30. The method according to claim 27, wherein the substance includes amyloid beta, and wherein activating the control circuitry comprises activating the control circuitry to drive the parenchymal electrode and the first CSF electrode to drive the amyloid beta from the brain parenchyma into the CSF-filled space of the brain, and to apply the treatment direct current between the second CSF electrode and the midplane treatment electrode to drive the amyloid beta from the CSF-filled space of the brain to the superior sagittal sinus.

31. The method according to claim 27, wherein the substance includes metal ions, and wherein activating the control circuitry comprises activating the control circuitry to drive the parenchymal electrode and the first CSF electrode to drive the metal ions from the brain parenchyma into the CSF-filled space of the brain, and to apply the treatment direct current between the second CSF electrode and the midplane treatment electrode to drive the metal ions from the CSF-filled space of the brain to the superior sagittal sinus.

32. The method according to claim 27, wherein the substance includes tau protein, and wherein activating the control circuitry comprises activating the control circuitry to drive the parenchymal electrode and the first CSF electrode to drive the tau protein from the brain parenchyma into the CSF-filled space of the brain, and to apply the treatment direct current between the second CSF electrode and the midplane treatment electrode to drive the tau protein from the CSF-filled space of the brain to the superior sagittal sinus.

* * * * *